US010737124B2

(12) United States Patent
Lal

(10) Patent No.: US 10,737,124 B2
(45) Date of Patent: Aug. 11, 2020

(54) ELECTRO-ULTRASONIC DEVICES FOR NERVE STIMULATION AND TREATMENT

(71) Applicant: Cornell University, Ithaca, NY (US)

(72) Inventor: Amit Lal, Ithaca, NY (US)

(73) Assignee: Cornell University, Ithaca, NY (US)

(*) Notice: Subject to any disclaimer, the term of this patent is extended or adjusted under 35 U.S.C. 154(b) by 1153 days.

(21) Appl. No.: 15/072,232

(22) Filed: Mar. 16, 2016

(65) Prior Publication Data

US 2016/0271427 A1    Sep. 22, 2016

Related U.S. Application Data

(60) Provisional application No. 62/133,982, filed on Mar. 16, 2015.

(51) Int. Cl.
*A61N 7/00* (2006.01)
*A61N 2/00* (2006.01)
*A61N 7/02* (2006.01)
*A61N 1/00* (2006.01)

(52) U.S. Cl.
CPC .............. *A61N 7/00* (2013.01); *A61N 1/00* (2013.01); *A61N 2/002* (2013.01); *A61N 2/006* (2013.01); *A61N 7/02* (2013.01); *A61N 2007/0026* (2013.01); *A61N 2007/0073* (2013.01); *A61N 2007/0095* (2013.01)

(58) Field of Classification Search
None
See application file for complete search history.

(56) References Cited

U.S. PATENT DOCUMENTS

| 6,740,058 | B2 | 5/2004 | Lal et al. | |
| 8,197,418 | B2 | 6/2012 | Lal et al. | |
| 8,774,928 | B2* | 7/2014 | Towe | A61N 1/32 607/48 |
| 2008/0018199 | A1* | 1/2008 | Trolier-McKinstry | B06B 1/0629 310/311 |
| 2012/0290023 | A1* | 11/2012 | Boyden | A61N 5/025 607/3 |
| 2013/0300204 | A1* | 11/2013 | Partovi | H01F 38/14 307/104 |

(Continued)

OTHER PUBLICATIONS

Anderson, J.M., "Biological responses to materials," Annual Review of Materials Science, vol. 31, pp. 81-110, 2001.

(Continued)

*Primary Examiner* — Boniface N Nganga
(74) *Attorney, Agent, or Firm* — Perkins Coie LLP

(57) ABSTRACT

Methods, systems, and devices are disclosed for acoustic nerve stimulation. In one aspect, a system for acoustic nerve stimulation is disclosed. The system comprises an ultrasonic phased array chip device deployable into a living organism, the ultrasonic phased array chip device including a substrate and an acoustic signaling module on the substrate that includes an array of acoustic transducer elements operable to generate ultrasonic beams based on electronic control signals, capable to propagate the ultrasonic beams through biological nervous tissue to affect nervous signal firing; and a transmitter device wearable on an exterior of the living organism, wirelessly couplable with the ultrasonic phased array chip device to transmit the electronic control signals.

21 Claims, 19 Drawing Sheets

(56) References Cited

U.S. PATENT DOCUMENTS

| | | | |
|---|---|---|---|
| 2014/0058292 A1* | 2/2014 | Alford | A61N 7/00 601/2 |
| 2014/0094674 A1* | 4/2014 | Nurmikko | A61B 5/04001 600/378 |
| 2016/0220828 A1* | 8/2016 | Yan Poon | A61N 1/3787 |
| 2017/0080255 A1* | 3/2017 | Law | G01S 7/521 |

OTHER PUBLICATIONS

Ardanuc, S. et al., "PZT driven micromachined 2-D membrane arrays," in 2004 IEEE Ultrasonics Symposium, Aug. 23, 2004-Aug. 27, 2004, Montreal, Que., Canada, 2004, pp. 509-512.

Ardanuc, S. et al., "Ultrasound enhanced electrostatic batch assembly for MEMS," Sensors and Actuators A (Physical), vol. 197, pp. 136-149, Aug. 2013 2013.

Ardanuc, S. et al., "Bulk detection of sound waves launched by surface micromachined beam resonators," in 2005 IEEE Ultrasonics Symposium, Sep. 18, 2005-Sep. 21, 2005, Rotterdam, Netherlands, 2005, pp. 1171-1174.

Arias, M. et al., "A Piezoelectric Material P(VDF-TrFE) Thin-Film )rocess Flow for Ultrasonic Transducers" Cornell University, NNIN2014.

Bachtold, M.R. et al., "Focused ultrasound modifications of neural circuit activity in a mammalian brain," Ultrasound in Medicine and Biology, vol. 24, pp. 557-565, May 1998.

Ben-Menachem, E. et al., "Preliminary experience with a new system for vagus nerve stimulation for the treatment of refractory focal onset seizures," Epilepsy & Behavior, vol. 29, pp. 416-419, 2013/Nov. 2013.

Bessa, J.M., et al., "A trans-dimensional approach to the behavioral aspects of depression," Front Behav Neurosci, vol. 3, p. 1, 2009.

Carson, P.L. et al., "Ultrasonic power and intensities produced by diagnostic ultrasound equipment," Ultrasound in Medicine & Biology, vol. 3, pp. 341-350, 1978.

Chen, P.-C. et al., "Ultrasonically actuated inserted neural probes for increased recording reliability," in 2013 Transducers Eurosensors XXVII: The 17th International Conference on Solid-State Sensors, Actuators and Microsystems (Transducers Eurosensors XVII), 2013, pp. 872-875.

Chen. X. et al., "Integrated pressure and flow sensor in silicon-based ultrasonic surgical actuator," in 2001 Ultrasonics Symposium, Oct. 6, 2001-Oct. 10, 2001, Atlanta, GA, United states, 2001, pp. 1373-1376.

Chen, X. et al., "Ultrasonically actuated silicon microprobes for cardiac signal recording," IEEE Transactions on Biomedical Engineering, vol. 53, pp. 1665-1671, 2006.

Colucci, V. et al., "Focused ultrasound effects on nerve action potential in vitro," Ultrasound in medicine & biology, vol. 35, pp. 1737-1747, Aug. 3, 2009.

Dlouhy, B. et al., "Vagus nerve stimulation after lead revision," Neurosurgical Focus, vol. 32, p. E11, 2012.

Duman, C.H., "Models of depression," Vitam Horm, vol. 82, pp. 1-21, 2010.

Ferrari, G.M.D. et al., "Chronic vagus nerve stimulation: a new and promising therapeutic approach for chronic heart failure," European Heart Journal, vol. 32, pp. 847-855, Apr. 1, 2011/ 2011.

Ferrari, G.M.D. et al., "Vagus nerve stimulation: from pre-clinical to clinical application: challenges and future directions," Heart Failure Reviews, vol. 16, pp. 195-203, Dec. 17, 2010/ 2010.

Fry, W.J., "Electrical stimulation of brain localized without probes—theoretical analysis of a proposed method," The Journal of the Acoustical Society of America, vol. 44, pp. 919-931, Oct. 1968/ 1968.

Fry, W., "Action of Ultrasound on Nerve Tissue—a Review," Journal of the Acoustical Society of America, vol. 25, pp. 1-5, Jan. 1953.

Gavrilov, L.R. et al., "Application of focused ultrasound for the stimulation of neural structures," Ultrasound in Medicine & Biology, vol. 22, pp. 179-192, // 1996.

Greisen, M.H. et al., "Cholecystokinin tetrapeptide effects on HPA axis function and elevated plus maze behaviour in maternally separated and handled rats," Behav Brain Res, vol. 161, pp. 204-212, Jun. 20, 2005.

Hassanzadeh, R. et al., "Neuromodulation for Intractable Headaches," Current Pain and Headache Reports, vol. 18, pp. 1-8, Feb. 2, 2014/ 2014.

Henderson, J. et al., "A survey of the acoustic outputs of diagnostic ultrasound equipment in current clinical use," Ultrasound in Medicine & Biology, vol. 21, pp. 699-705, / 1995.

Hiroi, R. et al., "Differential effects of ovarian steroids on anxiety versus fear as measured by open field test and fear-potentiated startle," Behav Brain Res, vol. 166, pp. 93-100, Jan. 6, 2006.

Hoople, J. et al., "Chip-scale reconfigurable phased-array sonic communication," in Ultrasonics Symposium (IUS), 2014 IEEE International, 2014, pp. 479-482.

Hoople, J. et al., "Chip-scale sonic communication using AlN transducers," in Ultrasonics Symposium (IUS), 2013 IEEE International, 2013, pp. 1934-1937.

Howland, R.H., "Vagus Nerve Stimulation," Current Behavioral Neuroscience Reports, vol. 1, pp. 64-73, Mar. 7, 2014/ 2014.

Ito, K. et al., "Measurement of acoustic impedance for normal, fibrosis and NASH livers by using bio-acoustic microsropy," in 2014 IEEE International Ultrasonics Symposium (IUS), Sep. 3-6, 2014, Piscataway, NJ, USA, 2014, pp. 2382-2385.

Johns, L.D., "Nonthermal Effects of Therapeutic Ultrasound: The Frequency Resonance Hypothesis," Journal of Athletic Training, vol. 37, pp. 293-299, Jul.-Sep. 2002.

Kaajakari, V. et al., "Parametric excitation of circular micromachined polycrystalline silicon disks," Applied Physics Letters, vol. 85, pp. 3923-3925, 2004.

Kaajakari, V. et al., "Micromachined ultrasonic motor based on parametric polycrystalline silicon plate excitation," Sensors and Actuators, A: Physical, vol. 137, pp. 120-128, 2007.

Knappertz, V.A. et al., "Vagus nerve imaging with ultrasound: anatomic and in vivo validation," Otolaryngol Head Neck Surg, vol. 118, pp. 82-85, Jan. 1998.

Kotani, K. et al., "High efficiency CMOS rectifier circuit with self Vth cancellation and power regulation functions for UHF RFIDs," in IEEE ASSCC, 2007.

Kraus, T. et al., "CNS BOLD fMRI Effects of Sham-Controlled Transcutaneous Electrical Nerve Stimulation in the Left Outer Auditory Canal—A Pilot Study," Brain Stimulation, vol. 6, pp. 798-804, Sep. 2013/2013.

Kuo, J. et al., "Towards ultrasonic through-silicon vias (UTSV)," in Ultrasonics Symposium (IUS), 2014 IEEE International, 2014, pp. 483-486.

Lal, A. et al., "Silicon microfabricated horns for power ultrasonics," Sensors and Actuators, A: Physical, vol. 54, pp. 542-546, 1996.

Lee, C. et al., "A Sub-threshold Voltage Ladder Rectifier for Orthogonal Current-reuse Neural Amplifier," in IEEE BioCAS, 2013.

Legon, W. et al., "Transcranial focused ultrasound modulates the activity of primary somatosensory cortex in humans," Nat Neurosci, vol. 17, pp. 322-329, 02//print 2014.

Liu, L., et al., "Transient gastric irritation in the neonatal rats leads to changes in hypothalamic CRF expression, depression- and anxiety-like behavior as adults," PLoS One, vol. 6, p. e19498, 2011.

Loeb, G. et al., "BION system for distributed neural prosthetic interfaces," Medical Engineering & Physics, vol. 23, pp. 9-28, 2001.

Martin, E.M. et al., "Ultrasound-induced Contraction of the Carotid Artery in vitro," Ultrasound in Medicine and Biology, vol. 36, pp. 166-172, 2010.

Menz, M.D. et al., "Precise neural stimulation in the retina using focused ultrasound," J Neurosci, vol. 33, pp. 4550-4560, Mar. 6, 2013.

Mihran, R.T. et al., "Temporally-specific modification of myelinated axon excitability in vitro following a single ultrasound pulse," Ultrasound in medicine & biology, vol. 16, pp. 297-309, 1990.

Muratore, R. et al., "Hippocampal culture stimulus with 4-megahertz ultrasound," in 11th International Symposium on Therapeutic Ultrasound, Apr. 11-13, 2011, USA, 2012, pp. 254-258.

(56) References Cited

OTHER PUBLICATIONS

Nabibekov, M.K. et al., "Study of ultrasonic cutting of soft biotissues," Mechanics of Composite Materials, vol. 16, pp. 377-382, May 1, 1980/ 1980.

Nadig, S. et al., "Monolithic piezoelectric in-plane motion stage with low cross-axis-coupling," in 27th IEEE International Conference on Micro Electro Mechanical Systems, MEMS 2014, Jan. 26, 2014-Jan. 30, 2014, San Francisco, CA, United states, 2014, pp. 524-527.

Norton, S.J., "Can ultrasound be used to stimulate nerve tissue?," BioMedical Engineering OnLine, vol. 2, Mar. 4, 2003/2003.

Plaksin, M. et al., "Intramembrane Cavitation as a Predictive Bio-Piezoelectric Mechanism for Ultrasonic Brain Stimulation," Physical Review X, vol. 4, Jan. 21, 2014/ 2014.

Saijo, Y. et al., "Ultrasonic tissue characterization of infarcted myocardium by scanning acoustic microscopy," Ultrasound in Medicine and Biology, vol. 23, pp. 77-85, / 1997.

Sharp, A.A. et al., "In Vivo Penetration Mechanics and Mechanical Properties of Mouse Brain Tissue at Micrometer Scales," IEEE Transactions on Biomedical Engineering, vol. 56, pp. 45-53, Jan. 2009/2009.

Shen, C.-P., "Silicon Based Co-Integrated Bioelectrical and Biomechanical Interfaces: Applications to Insect Olfactory Neural Interfaces, Miniature Neural Interfaces, and Cardiac Excitation Characterization," Jan. 31, 2012/ 2012.

Slawecki, C.J., "Comparison of anxiety-like behavior in adolescent and adult Sprague-Dawley rats," Behav Neurosci, vol. 119, pp. 1477-1483, Dec. 2005.

Son, I.-S. et al., "A multifunctional silicon-based microscale surgical system," Sensors and Actuators, A: Physical, vol. 1, pp. 351-356, 2001.

Strekalova, T. et al., "Stress-induced anhedonia in mice is associated with deficits in forced swimming and exploration," Neuropsychopharmacology, vol. 29, pp. 2007-2017, Nov. 2004.

Sukharev, S. et al., "Mechanosensitive Channels: Multiplicity of Families and Gating Paradigms," Science Signaling, vol. 2004, pp. re4-re4, Feb. 10, 2004/ 2004.

Terry. R.S. et al., "The Implantable Neurocybernetic Prosthesis System," Pacing and Clinical Electrophysiology, vol. 14, pp. 86-93, 1991.

Tsui, et al., "In vitro effects of ultrasound with different energies on the conduction properties of neural tissue," Ultrasonics, vol. 43, pp. 560-565, 2005.

Tyler, W.J., "Noninvasive Neuromodulation with Ultrasound? A Continuum Mechanics Hypothesis," The Neuroscientist, vol. 17, pp. 25-36, 2011.

Tyler, W.J. et al., "Remote excitation of neuronal circuits using low-intensity, low-frequency ultrasound," PLoS One, vol. 3, p. e3511, 2008.

Velling, V.A. et al., "Modulation of the functional state of the brain with the aid of focused ultrasonic action," Neuroscience and Behavioral Physiology, vol. 18, pp. 369-375, Sep. 1, 1988/ 1988.

Ventureyra, E.C.G., "Transcutaneous vagus nerve stimulation for partial onset seizure therapy," Child's Nervous System, vol. 16, pp. 101-102, 2000.

Walf, A.A. et al., "The use of the elevated plus maze as an assay of anxiety-related behavior in rodents," Nat Protoc, vol. 2, pp. 322-328, 2007.

Wang, X., et al., "Metabonomics approach to understanding acute and chronic stress in rat models," J Proteome Res, vol. 8, pp. 2511-2518, May 2009.

Willner, P., "Chronic mild stress (CMS) revisited: consistency and behavioural-neurobiological concordance in the effects of CMS," Neuropsychobiology, vol. 52, pp. 90-110, 2005.

Wulff, V.J. et al., "Effects of Ultrasonic Vibrations on Nerve Tissues," Experimental Biology and Medicine, vol. 76, pp. 361-366, 1951.

Yamakawa, K. et al., "Electrical Vagus Nerve Stimulation Attenuates Systemic Inflammation and Improves Survival in a Rat Heatstroke Model," PLoS ONE, vol. 8, p. e56728, 2013.

\* cited by examiner

US 10,737,124 B2

ELECTRO-ULTRASONIC DEVICES FOR NERVE STIMULATION AND TREATMENT

PRIORITY CLAIM AND RELATED PATENT APPLICATION

This patent document claims priority and the benefits of U.S. Provisional Application No. 62/133,982 entitled "ELECTRO-ULTRASONIC DEVICES FOR NERVE STIMULATION AND TREATMENT" and filed Mar. 16, 2015, the disclosure of which is incorporated by reference as part of the specification of this document.

TECHNICAL FIELD

This patent document relates to systems, devices, and processes that use electro-acoustic technologies.

BACKGROUND

Semiconductor fabrication and nanotechnology provide techniques or processes for fabricating structures, devices, and systems with features at a micro- or nano-scale, e.g., structures in a range of one to hundreds of nanometers in some applications. Integrated circuits and microprocessors are examples of such structures, devices and systems.

Complementary metal-oxide-semiconductor (CMOS) technology is used in integrated circuits for a wide variety of devices. For example, CMOS design can include complementary and symmetrical pairs of p-type and n-type metal oxide semiconductor field effect transistors (MOSFETs) for logic functions. CMOS technology is used for digital circuit devices including microprocessors, microcontrollers, memory, and other digital logic circuits. CMOS technology is also used for analog circuits including image sensors, data converters, and highly integrated transceivers, among others. CMOS technology allows for a high density of logic functions on a chip. CMOS devices can exhibit desirable performance properties including, for example, high noise immunity and low static power consumption.

SUMMARY

Disclosed are injectable electrically transduced ultrasonic devices to deliver ultrasonic acoustic energy to the nerve structures (e.g., such as the vagus nerve) for treatment of a variety of conditions, including PTSD (Post Traumatic Stress Disorder), mental depression, chronic pain, and autoimmune diseases.

In implementations of the disclosed technology, the disclosed devices can generate a bio-interface between the devices and nerve fibers based on SPARCs (Sonic Phased Arrays Chips) to provide ultrasonic pulse based modulation of nerve firing rates. In some implementations, the SPARC microchips are delivered directly to the target nerve by injection in solution using an ultrasonically actuated needle that allows for clog-free and electronically controlled delivery of SPARCs under guidance by ultrasound imaging, thereby eliminating the need for surgery.

In one example aspect, a system for acoustic nerve stimulation is disclosed. The system comprises an ultrasonic phased array chip device deployable into a living organism, the ultrasonic phased array chip device including a substrate and an acoustic signaling module on the substrate that includes an array of acoustic transducer elements operable to generate ultrasonic beams based on electronic control signals, capable to propagate the ultrasonic beams through biological nervous tissue to affect nervous signal firing, and a transmitter device wearable on an exterior of the living organism, wirelessly couplable with the ultrasonic phased array chip device to transmit the electronic control signals.

In another example aspect, a method for acoustic nerve stimulation is disclosed. The method comprises transmitting, from a transmitter device positioned on an exterior surface of a living organism, an electronic control signal to a phased array chip device comprising an array of acoustic transducer elements; generating, by the array of acoustic transducer elements, based on the control signal, one or more ultrasonic beams; and causing the one or more ultrasonic beams to propagate through biological nervous tissue of the living organism to an area near a nerve of the living organism to affect nervous signal firing.

In another example aspect, an ultrasonic phased array chip for acoustic nerve stimulation is disclosed. The ultrasonic phased array chip comprises a substrate and an array of acoustic transducer elements on the substrate, the array being operable to generate ultrasonic beams capable of affecting signal firing of a target nerve area.

BRIEF DESCRIPTION OF THE DRAWINGS

FIGS. 9(a)-9(e) show

DETAILED DESCRIPTION

Figure 1:
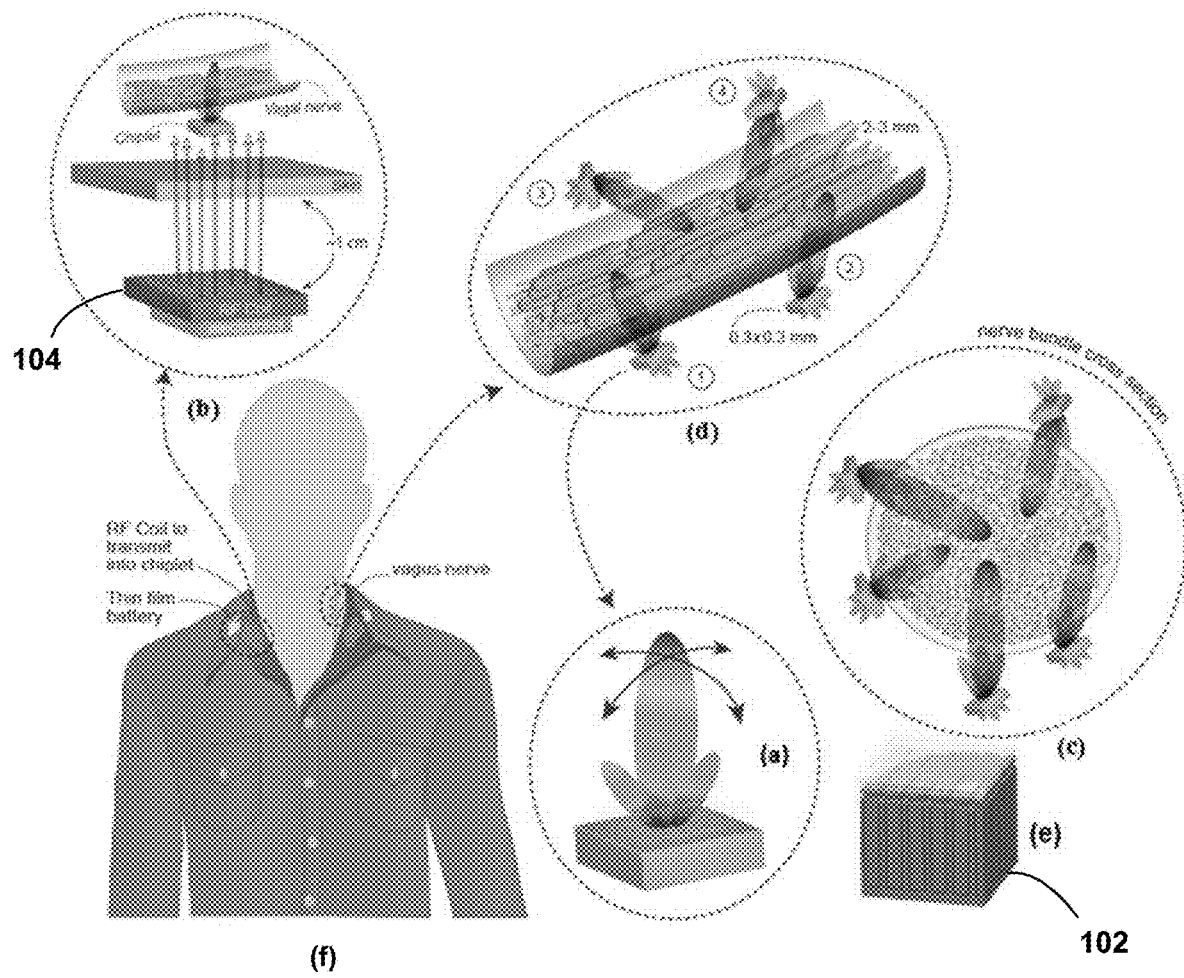
FIGS. 1(a)-1(f) show an exemplary embodiment for Vagus Nerve Ultrasonic Stimulation Therapy (VNUSx).

Disclosed are devices, systems, and methods for delivering and operating electrically transduced ultrasonic devices to provide ultrasonic acoustic energy to the nerve structures (e.g., such as the vagus nerve) for treatment of a variety of conditions, including PTSD (Post Traumatic Stress Disorder), mental depression, chronic pain, and auto-immune diseases.

FIGS. 1(a)-1(f) show one example embodiment of the disclosed electrically transduced ultrasonic devices, depicting an exemplary implementation of the disclosed devices for Vagus nerve ultrasonic stimulation therapy (VNUSx). FIG. 1(a) shows an illustrative diagram of an example Sonic Phased Array Chip (SPARC) that are injected near the Vagus nerve using an injection as shown in FIG. 1(d), e.g., without surgery. FIG. 1(b) shows an illustrative diagram of the exemplary device including collar-mounted RF antennas 104 to power SPARC and program SPARC chips. FIG. 1(c) shows an illustrative diagram of SPARCs in operation to scan an ultrasonic beam, providing focused energy at the axon level, or a group of axons. The sonic energy inhibits or increases nerve firing rates, through a number of mechanisms including direct strain, heat, radiation force, and cavitation. FIG. 1(d) shows an illustrative diagram of operation, e.g., in which many different diseases can be cured by targeted excitation of the Vagus nerve, in contract to all existing approaches. For example, SPARCs can be misaligned as in positions 1,2,3,4 and still be able to transmit ultrasound (US) pulses within the nerve. FIG. 1(e) shows an illustrative diagram cross section of an example SPARC chip 102 with buried capacitor, AlN transducers, bio-compatible passivation layer, and charging coil.

The disclosure of this patent document describes an electrically transduced ultrasonic energy based device, e.g., which can be implemented to treat some of the most pressing problems for war-fighters. For example, these include PTSD (Post Traumatic Stress Disorder), mental depression, and chronic pain, auto-immune diseases, when returning from war or special missions.

Recently, electrical stimulation of the Vagus nerve can be used to treat a variety of maladies. For example, FDA has approved VNS (Vagus Nerve Stimulation) as a therapy for diseases such as epilepsy. Such techniques involve only electrical stimulation of the nerves, which have been shown to effect Vagus nerve. The application of electrical stimulation requires a surgical procedure and an implant, both of which can be significant barriers to adoption, especially in diseases such as PTSD where patients may choose to live with the symptoms, or take oral medications, rather than undergo a treatment by surgery and face possible complications with surgery. Furthermore, even after surgery, the electrodes used for stimulation may not last forever, due to immune reaction induced buildup of insulating tissue on the electrodes.

The disclosed technology provides a non-surgical approach to nerve stimulation, a technology that could last the lifetime of the patient, for a low-barrier to adoption technology enabling therapy for warfighters and the public at large. We disclose to use ultrasonic pulse based modulation of nerve firing rates. Exemplary preliminary data shows that the ultrasonic pulses can modulate nerve firing rates.

Figure 2:
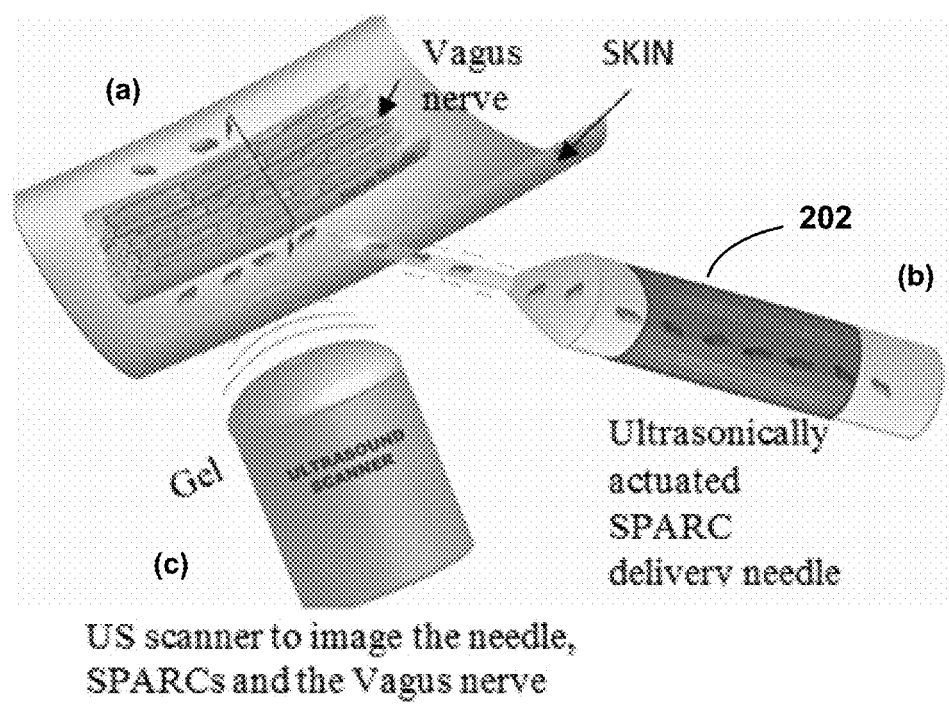
FIGS. 2(a)-2(c) show an exemplary ultrasonically driven needle used to deliver SPARCs across the skin near the Vagus nerve surface under ultrasonic imaging.

Exemplary embodiments of the disclosed devices can include the delivery of focused ultrasound (US) energy using Sonic Phased Arrays Chips (SPARCs), as depicted in FIG. 1. For example, delivering (e.g., injecting) the disclosed chip technology, e.g., such as 300×300×200 μm chip devices can be performed in a minimally invasive manner, such as shown in FIGS. 2(a)-2(c) . For example, using a hypodermic needle is a challenge, which we address by delivering the chiplets using an ultrasonically actuated needle 202 that allows for clog-free and electronically controlled delivery of SPARCs under guidance by ultrasound imaging. An exemplary ultrasonically actuated needle instrument for this purpose and the fundamental basis of sonically driven microfluidic delivery of SPARCs is further described in detail in U.S. Pat. No. 6,740,058, filed Jun. 8, 2001, by Amit Lal and Xi Chen, the disclosure of which is incorporated herein by reference. The disclosed injection approach will eliminate the need for surgery. Ultrasonically actuated needle can potentially reduce the pain of needle insertion, making the process of insertion even more simple.

SPARCs will enable application of ultrasonic pulses applying temporal strain on nerves to generate strains and strain gradients across the Vagus nerve by remotely RF power applied from outside the body, with RF generators attached to shirt collars near the Vagus nerve in the neck. This approach may allow the treatment of many diseases by stimulating specific sections of the Vagus nerve at different times. SPARC chips include state-of-art CMOS circuits to receive, store RF energy, and program and drive the integrated piezoelectric array. The SPARC chips can also be coated with biocompatible coatings to provide minimal immune activity and provide adhesion to tissue after insertion. A tremendous advantage of sonically induced nerve modulation is that the bio-interface between SPARC and the nerve may last much longer, perhaps a lifetime, as the sonic energy pulses can be transmitted though the tissue buildup, by adjusting frequencies and amplitude of the sonic pulses over time, as the body reaction to the implant stabilizes.

Wide Bandwidth Ultrasonic Transduction

The disclosed technology can include the use of bandwidths in selected ranges, e.g., from 10 MHz to 1 GHz. Such bandwidths can include not just many frequencies, but also the effect of combining different frequencies to modulate nerve. Higher frequencies give smaller localization of the ultrasonic field while suffering from higher absorption loss, requiring the placement of SPARC close to the nerves, while local frequencies provide non-specific excitation.

I. Vagus Nerve Stimulation

The vagus nerve is a major component of the autonomic nervous system, has an important role in the regulation of metabolic homeostasis, and plays a key role in the neuro-endocrine-immune axis to maintain homeostasis through its afferent (carrying information from the body to brain) and efferent (sending signals from the brain to the body) pathways. Vagus nerve stimulation (VNS) refers to any technique that stimulates vagus nerve, including manual or electrical stimulation and is approved in human for refectory epilepsy and depression. The most common clinical use of VNS involves the surgical implantation of a commercially available programmable pulse generator device (NCP System; Cyberonics, Inc., Houston, Tex., USA). A VNS device system (CardioFit System; BioControl Medical Ltd, Yehund, Israel) has been developed for the treatment of heart failure. The programmable device is implanted in the right chest wall. It is connected to the right cervical vagus using a cuff designed to preferentially activate vagal efferent fibers. The stimulator senses heart rate and shut off at a predetermined threshold of bradycardia. Preclinical studies and one phase II human study suggest that chronic right cervical VNS is safe and effective for treating heart failure. A similar VNS system (FitNeS System; BioControl Medical Ltd) has been designed with a cuff electrode that preferentially activates afferent fibers, which is intended to minimize typical VNS side effects related to efferent fiber stimulation. Left cervical VNS using this device has been described in five patients with epilepsy, who showed some benefit and no typical VNS side effects. A transcutaneous method of VNS (t-VNS) targets the cutaneous receptive field of the auricular branch of the vagus nerve. Applying an electrical stimulus to the left cymba conchae (using a stimulus intensity above the sensory detection threshold, but below the pain threshold) results in a brain activation pattern not dissimilar to that of left cervical VNS. The use of t-VNS for treating epilepsy was first proposed in 2000. Recently, a t-VNS (NEMOS; Cerbomed GmbH, Erlangen, Germany) received European clearance for the treatment of epilepsy and depression in 2010 and for the treatment of pain in 2012.

Figure 3:
FIG. 3 shows an exemplary non-invasive vagus nerve stimulator by gammaCore.

FIG. 3 shows another type of t-VNS device (gammaCore; electroCore LCC, Basking Ridge, N.J., USA) that has European clearance for the prophylactic and acute treatment of cluster headache, migraine, hemicranias continua, and medication overuse headache. Therapy using gammaCore. However, this device has not been investigated in epilepsy or depression, and is again delivering energy over a very broad area of the anatomy.

II. Ultrasonic Stimulation of Nerves

Ultrasound imaging is pervasive in medicine. In ultrasonic imaging tissue transducers work in the 1-10 MHz range, generating ultrasonic intensities of 10-100 mW/cm$^2$ for B-Mode and M-Mode imaging. The pressure amplitudes of a 0.3-5 MPa are generated at the focused point of a phased array of transducers. For pulsed Doppler intensities as high as 1000-2000 mW/cm$^2$ are used to measure sufficient scattered signal for velocity measurement. The intensities used in medicine have been determined to be safe as they do not appear to trigger any bio-physical effects in the body. As far back as 1950s investigators had noticed that increased ultrasonic amplitudes can be used to trigger nerve response. Very high intensity levels of 10-300 Watts/cm$^2$ of intensities were used to illicit response in nerves. Ultrasonic pulses can be used to trigger response in nerves, both to increase and decrease nerve firing rates. A selected summary of these results is shown in Table 1.

Figure 4:
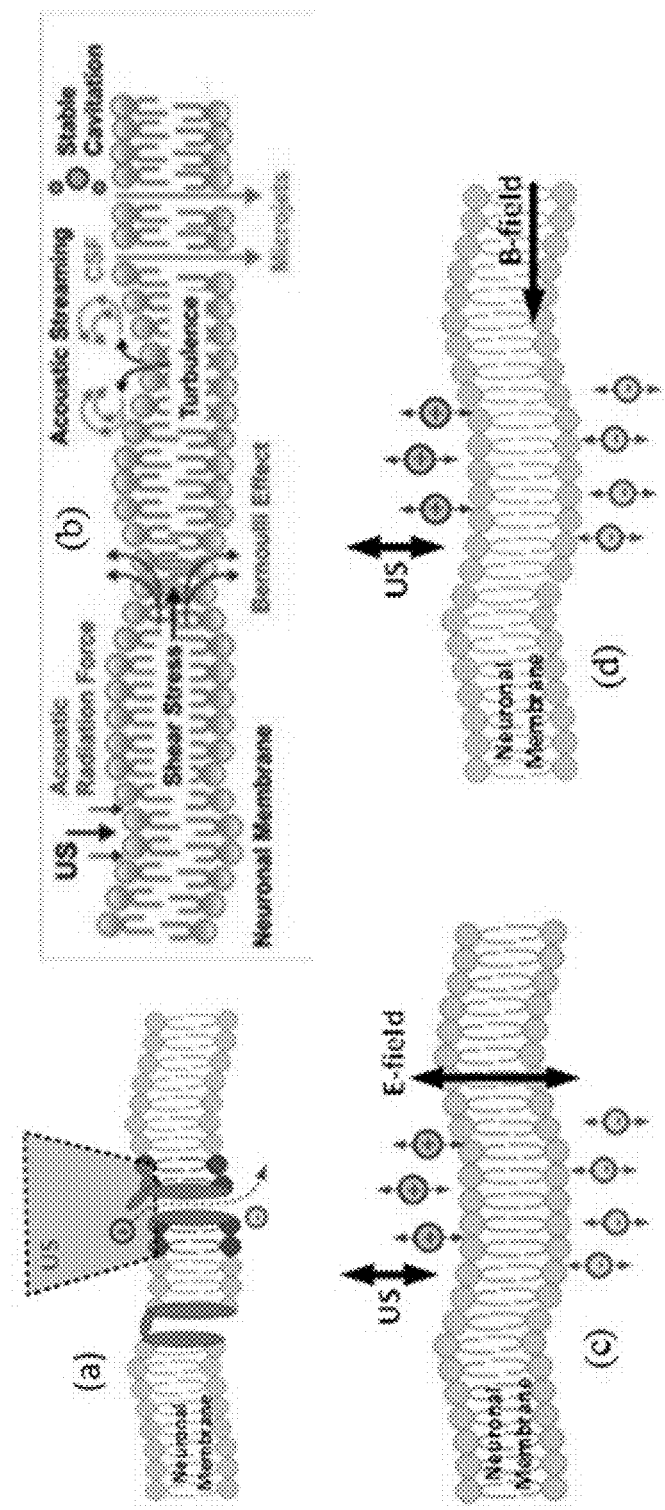
FIG. 4 shows some exemplary mechanisms of ultrasound-based nerve response.

FIG. 4 demonstrates many example mechanisms of US-based nerve response. These include:

Heating: A beam of ultrasound generates heat by absorption in the tissue both by both shear and bulk viscosity losses of the sinusoidal strain waves. The localized heat generated can raise temperatures to open ion channels for nerve triggering, as shown in FIG. 4(a).

Cavitation: Ultrasound-induced intramembrane cavitation within the bilayer membrane could underlie the biomechanics of a range of observed acoustic bio-effects. In central nervous system (CNS) neurons, ultrasound-induced cavitation of nanometric bilayer sonophores can induce a complex mechanoelectrical interplay leading to excitation, primarily through the effect of currents induced by membrane capacitance changes. FIG. 4(b) illustrates mechanisms of US based nerve response on acoustic radiation force, shear stress, acoustic streaming, and cavitation.

Direct ion-channel opening due to strain: Opening or closing of ion channels will alter their radius or hydrophobic thickness through conformational change, meaning that all of them will be to some extent sensitive to mechanical forces through the surrounding membrane or other sources, known as mechanosensitivity. It has been suggested that mechanical changes in membrane tension produced by ultrasound may increase the electrical activity of cells by altering ionic flux, as shown in FIG. 4(b).

Ultrasonic radiation force: Many of the voltage-gated ion channels (sodium, calcium, and potassium channels) expressed in neurons, as well as neurotransmitter receptors, possess mechanosensitive properties that render their gating kinetic sensitive to transient changes in lipid bilayer tension. Given that many voltage-gated ion channels possess some mechansosenstivity, acoustic radiation forces conferred by the action of ultrasound on lipid bilayers may lead to the opening of classic voltage-gated channels, as shown in FIG. 4(b).

Ultrasonic acoustic streaming: Combining a continuous extracellular space with the presence of both Newtonian (CSF) and non-Newtonian (viscoelastic cell membranes) fluids in the brain prompted formation of the continuum mechanics of ultrasonic neuro modulation. For example, it has been suggested that ultrasound can noninvasively modulate neuronal activity through a combination of pressure/fluid/membrane actions involving stable cavitation and acoustic streaming (micro jet formation, eddying and turbulence) in addition to acoustic radiation force, shear stress,

TABLE 1

| | | Ultrasonic nerve stimulation | |
|---|---|---|---|
| Intensity (W/cm$^2$) | Excitation Frequency | Tissue | Result/Comment |
| 0.03-30 | 43 MHz modulated at 0.5 Hz | Salamander retina | Ultrasound stimuli generated reproducible activity in retinal ganglion cells. Firing Threshold Level is found to be 0.75 and 0.25 W/cm2 during ultrasound turn on and off processes |
| Calculated highest dose is 0.4 W/cm$^2$ based on specified max pressure of 77 kPa | 4.04 MHz, 100 ms pulses | Rat hippocampal culture | Field potentials due to ultrasonic stimulus of different regions of the tissue were similar. |
| 100-800 | 2-7 MHz, 0.5 ms duration | Myelinated frog axon | Ultrasonic response and direct mechanical stimulation using stylus, showed similar response |
| 40-110 | 500 kHZ carrier at repetition rate of 200 kHz | Mammal hippocampal tissue | No cavitation is observed Overall response is found to be a combination of ultrasonic and thermal effects |

Bernoulli effects, and other fluid mechanical consequences, which stem from small acoustic impedance mismatches between lipid bilayers, surrounding intercellular/extracellular fluids, and interleaved cerebrovascular, as shown in FIG. 4(b).

Electric Field Augmented US: A method of transmitting ultrasound in the presence of an oscillating electric field of the same frequency has been proposed. The periodic variation of the electrical conductivity of the tissue created by the slight variation in thermal expansion arising from the oscillating sound wave would, in principle, produce a partial rectification of the applied field, resulting in a small amount of unidirectional electric current. The resulting unidirectional charge transfer could stimulate neural tissue, as shown in FIG. 4(c).

Magnetic field augmented US: A method of stimulating active tissue has been proposed by propagating ultrasound in the presence of a magnetic field. Since tissue is conductive, particle motion created by an ultrasonic wave will induce an electric current density generated by Lorentz forces. FIG. 4(d) shows that longitudinal particle motion due to ultrasonic wave moves the ions back and forth through the magnetic field. This results in Lorentz forces on the ions that give rise to an electric current density that oscillate at the ultrasonic frequency. This method could be used to locally stimulate active tissue by inducing an electric field in regions where the ultrasound is focused.

TABLE 2

Summary of many example mechanism of US-mediated nerve stimulation

| Effect | Physical effect | Measurement approach |
|---|---|---|
| Heating | Changes in baseline potential | IR camera, changes in resting potential, changes in action potential shapes |
| Cavitation | Double layer breakage due to cavitation, sound pulse, and possible light emission | Measurement of broadband sound waves, single-photon sensor, histology of nerves |
| Direct ion channel opening | Ion-channel strain to modulate opening/closing rates, rates should change linearly with voltage | Shape of the action potentials, modulate ion channels by ion channel inhibitors (e.g. acetylcholine) |
| Ultrasonic radiation force | Direct force stresses ion channel, intensity is square of drive voltage | Localized beams and use of voltage sensitive dyes |
| Ultrasonic acoustic streaming | Motion of fluid pockets can shear ion-channel | Fluorescent nanobead motion tracking |
| Electric Field Augmented US | Time averaged current in tissue due to self-rectification | Embedded probes inside nerve, as a function of external AC field |
| Magnetic field augmented US | Net current due to Lorentz force from US induced ion motion | Embedded probes inside nerve, as a function of external B-field |

III. Example Preliminary Results on Nerve Stimulation Using Our Own Transducers

TABLE 3

Action potential count under different ultrasound driving voltages

| $V_{pp}$ @ 100 kHz | Resonance Frequency | Exposure duration (sec) | Before count (Average) | During Count (Average) | % difference (during/before) | | |
|---|---|---|---|---|---|---|---|
| 1.6 | 105.59 | 0.6 | 32.57 | 39.03 | 19.86 | | |
| 1.57 | 104.90 | 0.6 | 46.9 | 55.47 | 18.27 | | |
| 2 | 105.57 | 0.6 | 16.87 | 19.93 | 18.18 | | |
| | 6.11 | | 105.37 | 0.6 | 31.83 | 44 | 38.22 |
| | 8 | | 105.31 | 0.6 | 33.33 | 39.23 | 17.7 |
| | 14 | | 105.17 | 0.6 | 12.53 | 16.57 | 32.18 |

Figure 5:
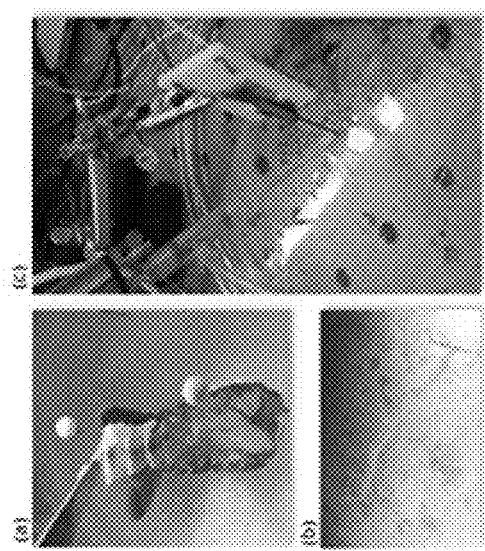
FIGS. 5(a)-5(d) show an exemplary setup used to measure effect of 100 kHz ultrasound on crayfish nerve.
Figure 5:
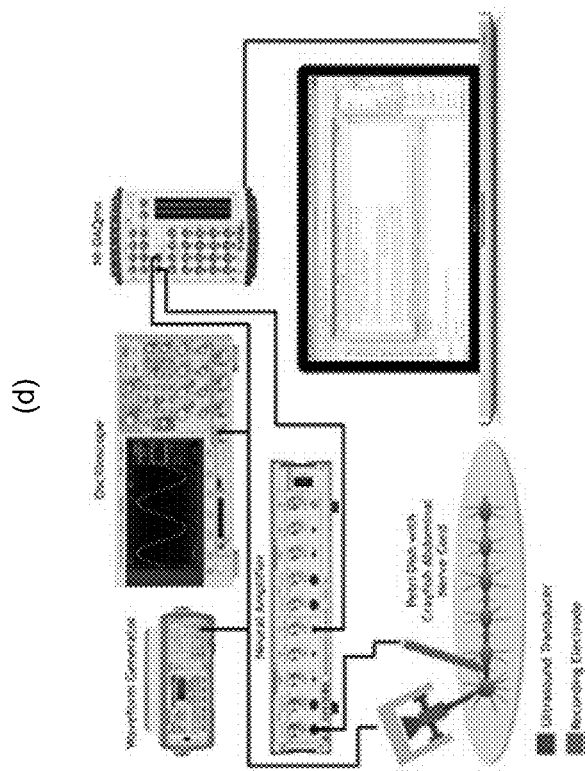
Figure 6:
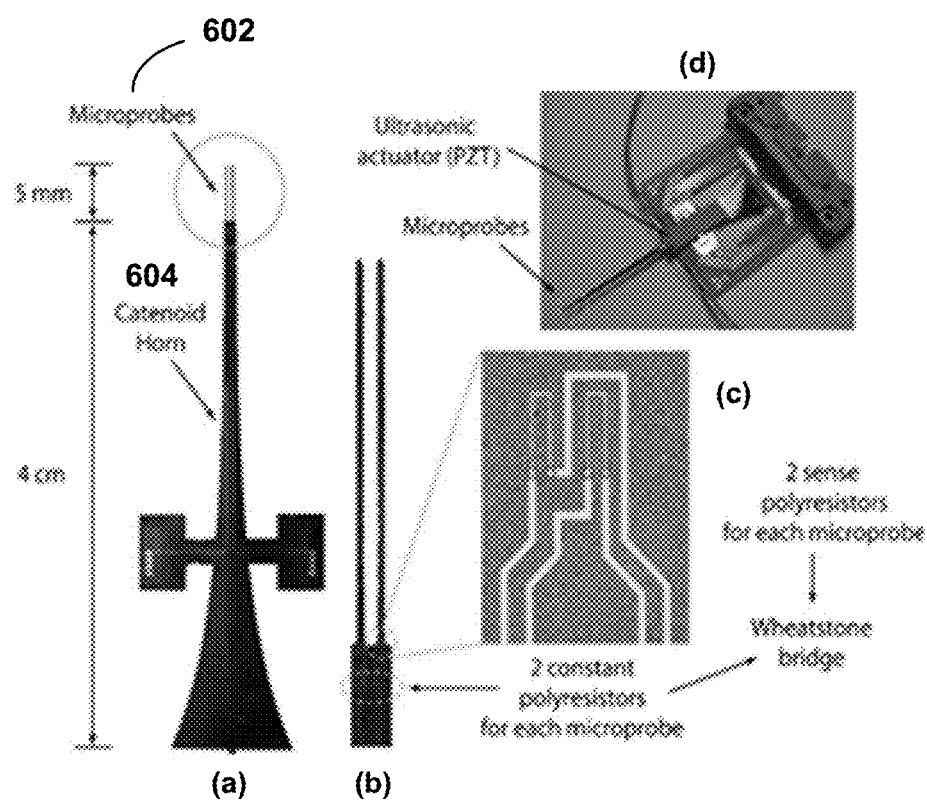
FIGS. 6(a)-6(d) show an exemplary silicon-horn transducer.

In some embodiments, US stimulation of unmyelinated nerves fiber from Large Red Crasyfish has been conducted. FIGS. 5(a)-5(d) show an example setup used to measure effect of 100 kHz US on crayfish nerve. FIG. 5(a), 5(b), 5(c) show the extracted nerve and the Si/PZT horn actuator.

Before each three second trial began, a 60 second delay was programmed in to allow of the nerves firing rate to return to baseline before moving forward. The sonic transducer was placed to stimulate the 6th abdominal ganglion with the recording electrode between the 5th and 6th ganglion. The ultrasonic stimulation protocol included recording the passive firing of a crayfish abdominal nerve cord for 1.5 seconds, then stimulating it with a 0.6 second ultrasonic pulse, followed by another 0.9 seconds of recordings without stimulation. During analysis, a consistent 0.47 second data sample was selected from before and during the stimulus. Prior to thresholding, a bandpass and bandstop filter was applied to reduce the coupling between the ultrasound signal and the action potentials. A threshold of 0.025 volts was used as a cutoff of signals we considered an action potentials. The action potential counts, averages, and percent difference before and during a stimulus is recorded in the Table 3. As can be seen, average pulse counts increased by 18% to 40%. These augmented stimulations occur with a relatively low intensity of 1.5-5 W/cm². Exemplary implementations can include testing at higher frequencies with AlN transducers.

IV. A Wideband Ultrasonic Stimulation Platform for Studying Ultrasonic Stimulation A comprehensive set of transducers that cover a wide range of frequencies and intensities have been developed. These transducers allow the investigation of nerve stimulation in a comprehensive design space of frequencies charting different effects of ultrasound. Driving a piezo transducer with sinusoidal voltage V at frequency ω, a plane wave with displacement, u, can be generated. The wave velocity is the time derivative of the displacement, assuming a linearized acoustic wave propagation equation $$v = \frac{du}{dt} = j\omega u_0 e^{-j(\omega t + kt)}.$$

The pressure in the wave is P=ρcv, where ρc is the tissue acoustic impedance. The intensity of the wave is $|I|=<P\cdot v>=<\rho c\cdot v^2>=\rho c(j\omega)^2 u_0^2 = \rho c\omega^2 u_0^2$. In the case of voltage limited operation, the displacement $u_0$ is generated by the piezoelectric actuator and can be written as $u_0=Qd_{33}V$, where $d_{33}$ is piezoelectric charge constant, and Q is the quality factor for the transducer. Therefore, The acoustic pressure and intensity can be written as $|P|=\rho c\omega Qd_{33}V$ and $|I|=\rho c\omega^2(Qd_{33}V)$. Net pressure from multiple transducers scales, adding in phase at a certain location, is $N\cdot \rho c\omega d_{33}V$, while the intensity scales as $\omega^2 (Nd_{33}V)^2$. This is the case for phased array operation where N actuators are driven at phases such that the pressure pulses add constructively at a location in space. For a fixed voltage drive, the intensity increases as the square of the frequency. The piezoelectric material that are most effective at high frequencies are Aluminum Nitride (AlN) and PVDF (Poly Vinyl DiFluoride) but have low piezoelectric coupling coefficients d33 ($d_{33}\sim 10^{-11}$ pC/N). PZT has a much greater d33 ($\sim 30*10^{-11}$ pC/N) but has a low quality factor at high frequencies due to internal losses between polycrystalline ceramic components that make up the material. At the SonicMEMS lab a family of ultrasonic actuators that have been developed to use all three piezoelectric materials—PZT, AlN, PVDF. Different transducer geometries are developed to achieve different results.

Silicon Horn Transducers (70-500 kHz): FIGS. 6(a)-6(d) show an example of silicon-horn transducer. A silicon horn is bulk-micromachined, with integrated strain gauges at the tip end. PZT plate 602 drives the horn in its longitudinal mode resonance. The piezorsistor sensor can provide feedback loop to control fix sonic intensity produced. The silicon-horn transducers are formed by attaching piezoelectric PZT to a silicon horn such that very high energy flux is available at the horn tip. The PZT plate (3 mm×5 mm×0.5 mm) is attached to the horn 604 at its ½-wavelgth node to maximize the coupling from the PZT into the silicon horn. The QK², or the product of the quality factor times the electromechanical coupling efficiency, is as high as 20-30 allowing very low voltage to couple substantial pressures into surrounding liquids. These transducers have been previously used for demonstrating low force insertion into tissue, probing tissue to measure tubule sizes using measured forces, measuring action potentials in the heart, as neural probes in mice and insect models, and reduced forces during surgery, and microsurgical tools. Some exemplary embodiments and the concept of force sensing to detect minute changes in mechanical properties of tissue are further described in more detail in U.S. patent No. 8,197,418, PCT No. PCT/US2008/066375, filed Jun. 9, 2008, by Amit Lal et al, the disclosure of which is incorporated herein by reference. The resonance frequencies of these transducers depends on the length of the horn as f_rx\frac{C}{2L} where c is the speed of sound of silicon. Probes have been designed ranging from 70 kHz (~8 cm long probes) to 500 kHz (~1 cm long probes). The shape of the horns magnifies the PZT generated motion and we have achieved motions as large at 1 um for 1 Vpp actuation at resonance frequencies for the longer probes. This motion can generate very high intensities for producing several non-linear effects including cavitation.

Figure 7:
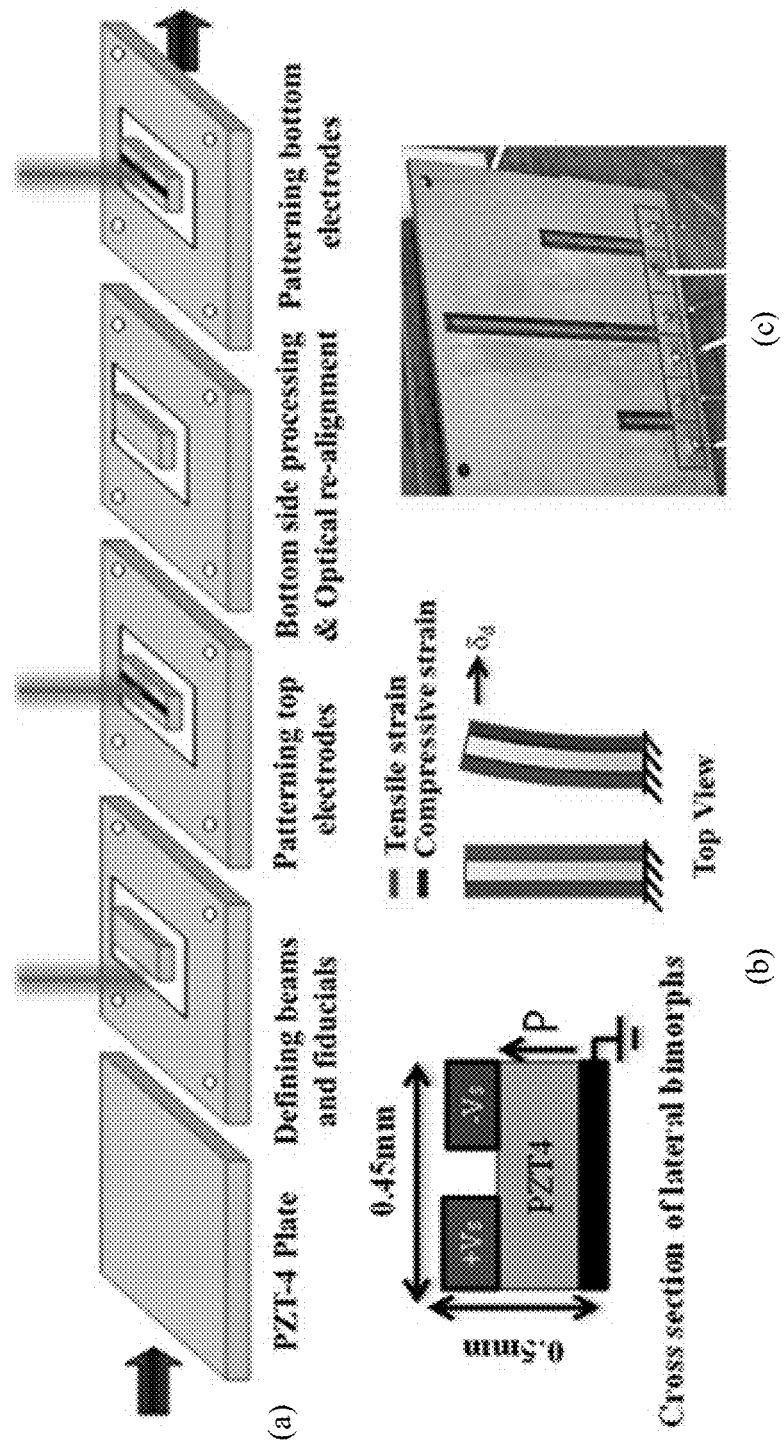
FIG. 7 shows an exemplary laser cutting fabrication sequence to realize 3D dimensional shapes of bulk-PZT plates.

PZT lateral bi-morph actuators (10-100 kHz): FIG. 7 shows a laser cutting fabrication sequence designed to realize 3D dimensional shapes of bulk-PZT plates, realizing thickness mode actuators that can be used for creating both ultrasonic and steady motion at near DC frequencies. FIG. 7(a) shows an exemplary fabrication process of laser cutting PZT structures. FIG. 7(b) shows the exemplary structure of the lateral bimorph. FIG. 7(c) shows exemplary fabricated lateral bimorphs with PZT alignment marks. By having two electrodes on two sides of a PZT beam, a bending motion is generated laterally. The lateral bimorph actuators then can be used to generate motion at very low frequencies of 5-100 kHz at CMOS compatible voltages.

Figure 8:
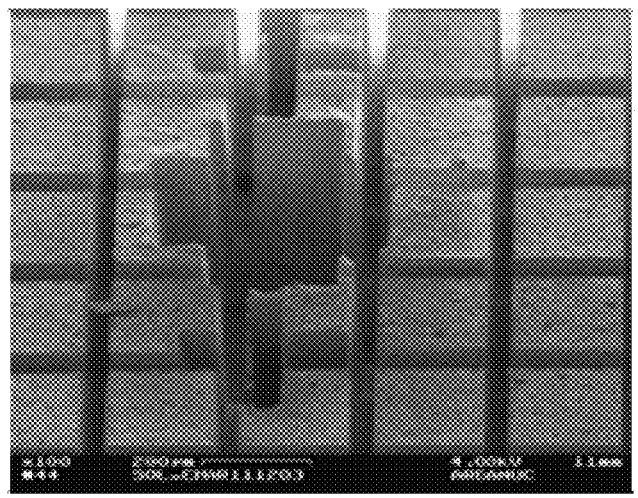
FIG. 8 shows an exemplary laser cut 2D array of PZT pixels.

PZT thickness mode actuators (500 kHz to 20 MHz): Machined PZT plates haven also been driven in their thickness mode resonances ranging from 3.3 MHz to 10 MHz when the PZT plates are 0.5 to 0.2 mm thick. FIG. 8 shows an exemplary laser cut 2D array of PZT pixels. PZT is 0.5 mm thick and a phased array operating at 3.3 MHz thickness mode resonances can be implemented using this array. These plates have been used to drive surface micro-machines and can reach high intensities of 50-100 W/cm² by virtue of high electromechanical coupling and quality factor.

Figure 9:
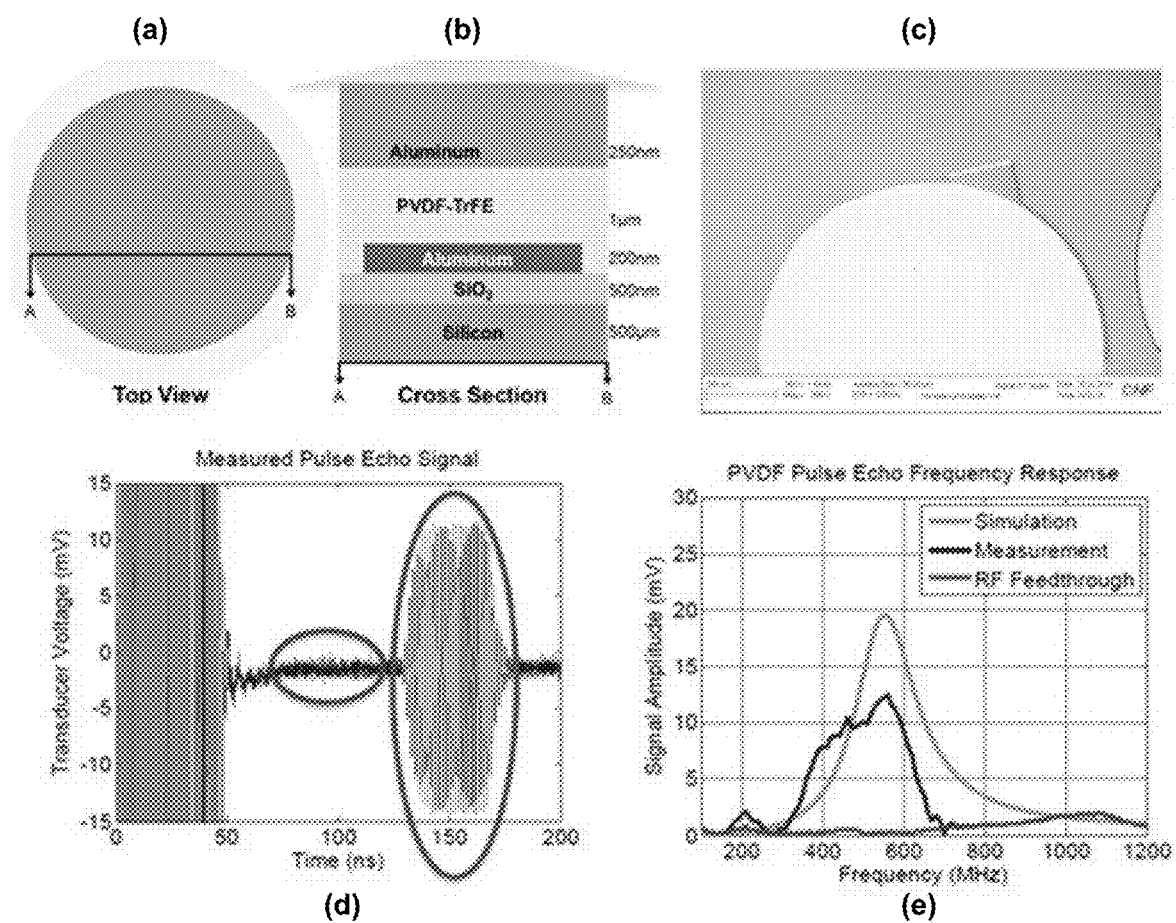
FIG. 9 shows an exemplary process flow to form PVDF polymer piezoelectric actuators.

Thin film PVDF actuators (50-500 MHz): FIGS. 9(a)-9(e) show an exemplary process flow to form PVDF polymer piezoelectric actuators. FIG. 9 indicates that SonicMEMS PVDF process flow is compatible with fabrication onto CMOS owing to the low temperature processing. In some embodiments, transducers have been made with operating range from 200-700 MHz with high electromechanical coupling efficiency. All materials used in this process are CMOS-compatible, which allows for fabrication of transducers directly with CMOS, greatly improving system complexity and integration. FIGS. 9(a)-9(e) further illustrate left and right cross sections of transducer. Layers in this process were defined using standard contact lithography. The process began with an insulating layer of 500 nm PECVD of $SiO_2$ on a 500 μm thick 4" wafer. Aluminum bottom and top electrodes of 210 nm and 250 nm respectively. P(VDF-TrFE) dissolved in 2-butanone (7.00% w/v) was deposited by spin coating to create a 1 μm thin layer, which was patterned using SPR 220-3.0 photoresist, and etched by dry oxygen plasma etch. After fabrication, an in situ electrical poling method was performed to induce piezoelectricity on the P(VDF-TrFE) film. An electrical field of 60 V/μm was applied on the transducer under 130° C. for one hour. These transducers have a high electromechanical coupling coefficient of 7-9% and have bandwidths extending from 100 to 600 MHz. What makes PVDF transducers especially important for ELECTRx is that the impedance of the material is closer to tissue impedance, enabling better coupling into tissue. In fact for the case of AlN transducers, we plan to use PVDF films to match to tissue at even higher frequencies.

Figure 10:
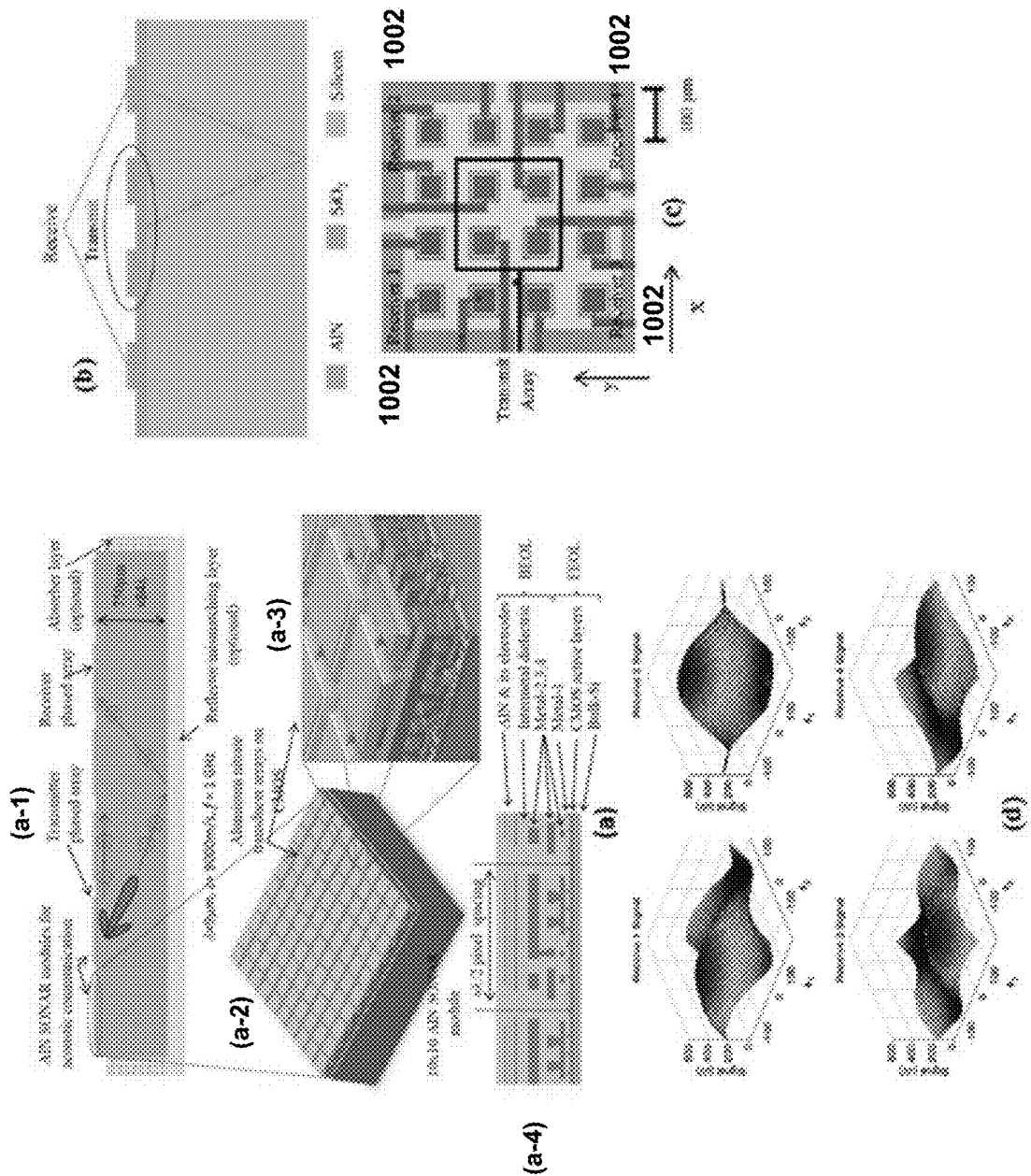
FIGS. 10(a-1)-10(a-4), (b), (c), and (d) show an exemplary sonar technology for performing on-chip ultrasonic communications using phased arrays of thin film piezoelectric pixels.

Aluminum Nitride High Frequency Transducers (500 MHz to 3 GHz): A sonar technology for performing on-chip ultrasonic communications using phased arrays of thin film piezoelectric pixels has been recently demonstrated. FIGS. 10(a-1)-10(a-4) show the overall AlN transducer architecture. Thin film AlN pixels are driven by embedded CMOS drivers for a single-chip sonic phased array. FIG. 10(b) shows the concept of sending pulses within silicon to communicate across chip using ultrasonic pulses. FIG. 10(c) and FIG. 10(d) show recent phased array testing where four pixels are phased to preferentially send data to one of four receivers 1002. The sound wavelength in silicon of 9 um at 1 GHz facilitates making many pixels and forming a phased array. The pixels are made to be in the 3-50 um in lateral dimensions and driven by different phases to form a sonar pulse that be shot at different directions. Coherent addition of pulses from 100s of pixels can greatly increase intensity even when these pixels are driven with CMOS compatible $1V_{pp}$ voltages. As part of the on-going I-APRA program TIC (Trusted Integrated Circuits), these arrays are being developed for intra-chip ultrasonic communication links such that the wires are virtual, hiding CMOS design chips. FIG. 10(d) shows how even four pixels can be used to communicate to neighboring pixels at bandwidths a high as 100 MHz. The scaling of CMOS allows for all of the electronics needed, phase shifters, amplifiers, receivers, to be integrated within the same chip. This technology allows the envisioning of the SPARCs for ELECTRX. Instead of shooting sonic pulses into silicon, there is plan to shoot pulses into surrounding the tissue and also into silicon so the pulses can be transmitted from the backside of the chips as well.

Each element in the array can be driven directly by low-voltage CMOS. This will require a phase rotator under each pixel, based on vector modulator topology. The input to each element is two LO signals offset by 90 degrees. Each of these signals is weighted and summed using the trigonometric relationship:

$$A\cos(x) + B\sin(x) = \sqrt{A^2 + B^2} \sin\left(x + \tan^{-1}\left(\frac{B}{A}\right)\right).$$

Figure 11:
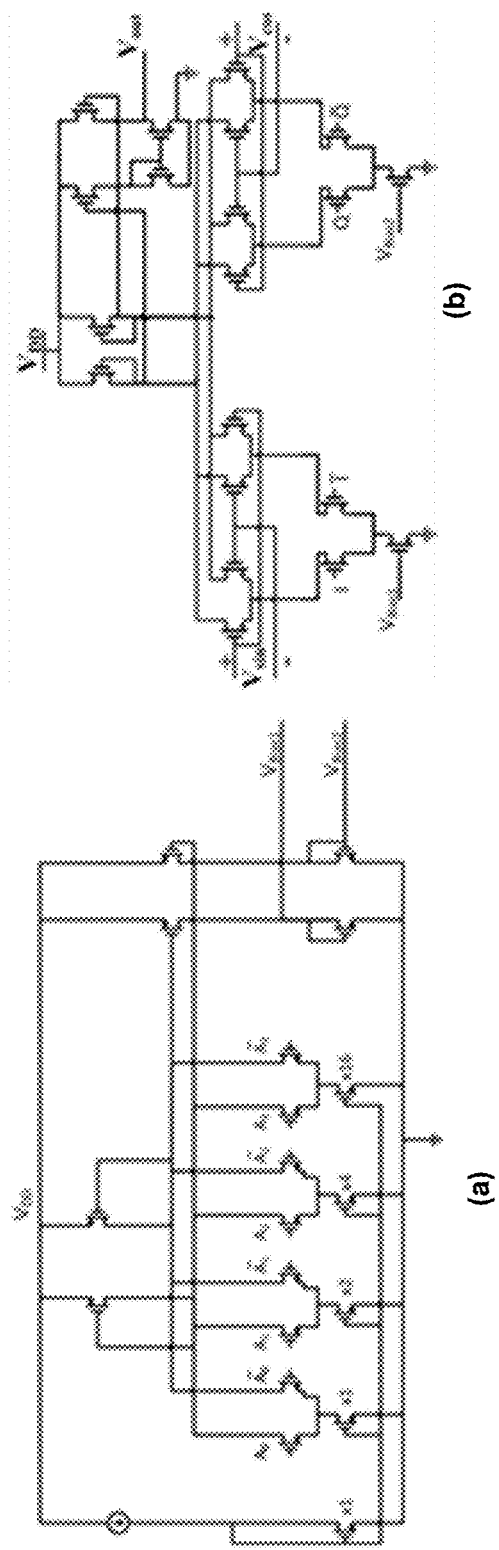
FIGS. 11(a)-11(b) show an exemplary schematic of single element phase rotator and DAC.

The weights, A and B are set by the current for each signal path. Using differential current ensures that the amplitude is fixed and the phase can be selected linearly. This is accomplished by a differential current DAC for each element. FIGS. 11(a)-11(b) show an exemplary schematic of single element phase rotator and DAC. Sin(wt) and Cos(wt) are multiplied by weights to achieve different phases needed for the phased array. The schematic in FIGS. 11(a)-11(b) allows for 6-bits of resolution or approximately 6 degrees of resolution. In a 28 nm process this circuit consumes approximately 25 μA with a 1 Volt power supply, for a total power of 25 microwatts per pixel. For a 10×10 array this is 2.5 mW.

TABLE 4

Family of SonicMEMS ultrasonic transducers

| Transducer family | Frequency Range | Nominal frequency | Dimensions | Applied Voltage (Vpp) | Transducer Q in tissue | Acoustic Intensity (W/cm$^2$) | Wavelength (~focal spot) (meters) | Absorption Depth in Tissue (dB/um) |
|---|---|---|---|---|---|---|---|---|
| AlN Phased arrays (10 × 10 array) | 500 MHz-3 GHz | 1 GHz | 300 × 300 um SPARC, 100 pixels | 0.2 | 5 | 59.2 | 1.50 × 10$^{-6}$ | 0.13 |
| PVDF Phased arrays (10 × 10 array) | 50 MHz-600 MHz | 200 MHz | 300 × 300 um SPARC, 100 pixels | 0.2 | 10 | 4.6 | 7.5 × 10$^{-6}$ | 5.23 × 10$^{-3}$ |
| PZT Thickness mode actuator | 500 kHz-50 MHz | 10 MHz | 300 × 300 um | 1 | 50 | 133.1 | 1.5 × 10$^{-4}$ | 1.35 × 10$^{-5}$ |
| Silicon/PZT Horn actuator | 70-500 kHz | 200 kHz | 1-10 cm long, 1 cm wide, 4 mm thick | 10 | 300 | 191.7 | 7.5 × 10$^{-3}$ | 5.x × 10$^{-9}$ |
| PZT Lateral bimorphs | 5-100 kHz | 40 kHz | 1-10 cm long, 1 mm wide, 0.5 mm thick | 10 | 300 | 7.7 | 3.75 × 10$^{-2}$ | 2.08 × 10$^{-10}$ |

The family of transducers described above is summarized in Table 4. Some embodiments cover a very broad frequency range of sonic transducers generating high intensity ultrasound pulses. Although a range of frequencies are possible with each variety, specific nominal frequencies are chosen for illustration of the ultrasonic intensities possible. For example, the SPARCS can focus the energy from an array of pixels (10×10) and generate acoustic intensities of 5-50 W/cm² at frequencies from 200 MHz to 1 GHz. The absorption of US in water, and hence tissue, can be approximated as $$I(x) = I_0 e^{-\alpha x}$$

where $$\alpha = \alpha_0 f^2$$

and $$\alpha_0 = 0.134 \frac{dB}{\mu m \cdot GHz^2} \text{ at } 40°C..$$

Even at 1 GHz, the absorption is 0.13 dB/μm. For a nerve bundle of 1-mm diameter, the US beam would propagate 20-30 um for a 3 dB reduction in intensity. With higher intensities we should be able to get trigger intensities even at 500 um depth. At the same time at lower frequencies of 200 MHz, the 3 dB distance is 500 um. Hence, SPARCS spaced around the nerve bundles should be able to scan and trigger nerve pulses with spatial accuracy of hitting one axon at a time. The transducers operating at lower frequencies can be used as SPARCs with a broader beam to expose the entire nerve to bias the strain. Furthermore, external transducers at even lower frequencies of 40-200 kHz can be used to create additional sonic strain into the tissue.

Figure 12:
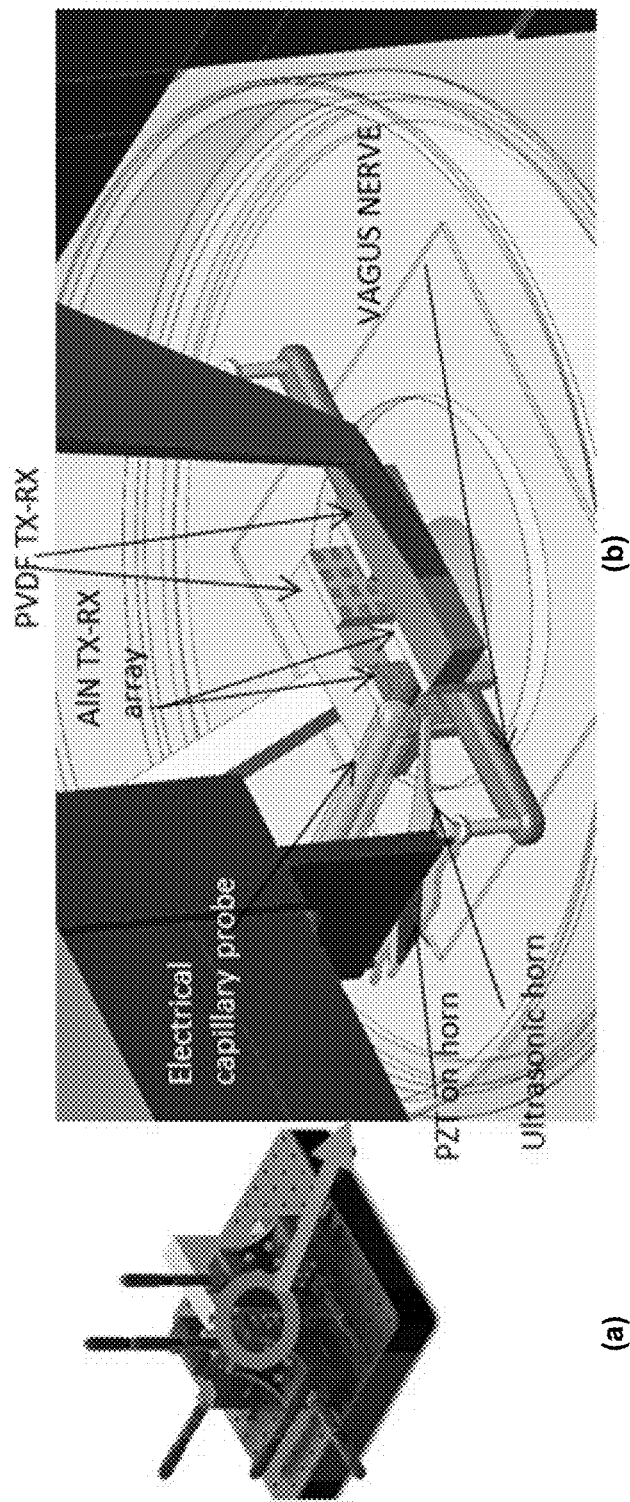
FIGS. 12(a)-12(b) show an exemplary setup to assemble the transducers.

An experimental setup of the assembled transducers is shown in FIG. 12. An in-vitro test setup is built where the extracted rat vagus nerve will be simultaneously exposed to ultrasonic transducers from 10 kHz to 1 GHz. Horn actuators and lateral bimorphs will generate low frequency ultrasound from 10 kHz to 500 kHz. PZT is used alone up to 10s of MHz, and PVDF and AlN thin film transducers to cover 100 MHz to 1 GHz. High frequency forces very close contact to nerves. Precision actuators will be used to aim wide bandwidth US exposure while measuring electrical activity from the nerve. IR cameras and single photon cameras will be used to monitor temperature and photon output due to possible cavitation events.

Characterization of tissue buildup: Due to the foreign body response, the SPARC transducer that are to be implanted into tissue will encapsulated in a dense layer of fibrotic connective tissue from collagen deposition. The fibrotic tissue properties varies depend on the surrounding tissue. For example, the fibrosis tissue for myocardium has been measured with bulk modulus of 3.12 GPa, density of 1.092 g/cm³, and the specific acoustic impedance of 1.85 MRayl. For example, the fibrosis liver tissue with acoustic impedance has been measured around 1.78 MRayl. The impedance mismatch between SPARC transducer won't reduce the effectiveness of the transducer efficiency too much compared to normal tissue with acoustic impedance around 1.5 MRayl.

V. SPARC CMOS Design

FIGS. 12(a)-12(b) show the disclosed electronic system of an individual SPARC. RF power is delivered through an integrated coil, and is rectified and boosted, and stored on a hold capacitor to provide DC voltage for the piezo-electric transducer driver circuits, as well as various low power auxiliary circuits. Those circuits include a signal detector, with rectifies and demodulates AM data riding on the RF signal to configure the delays of the transducer drivers. This circuitry also detects as triggering signal for stimulation pulses of ultrasound. During such stimulation, a limiter and programmable frequency divider are activated to provide the carrier wave for the transducer divers.

Figure 13:
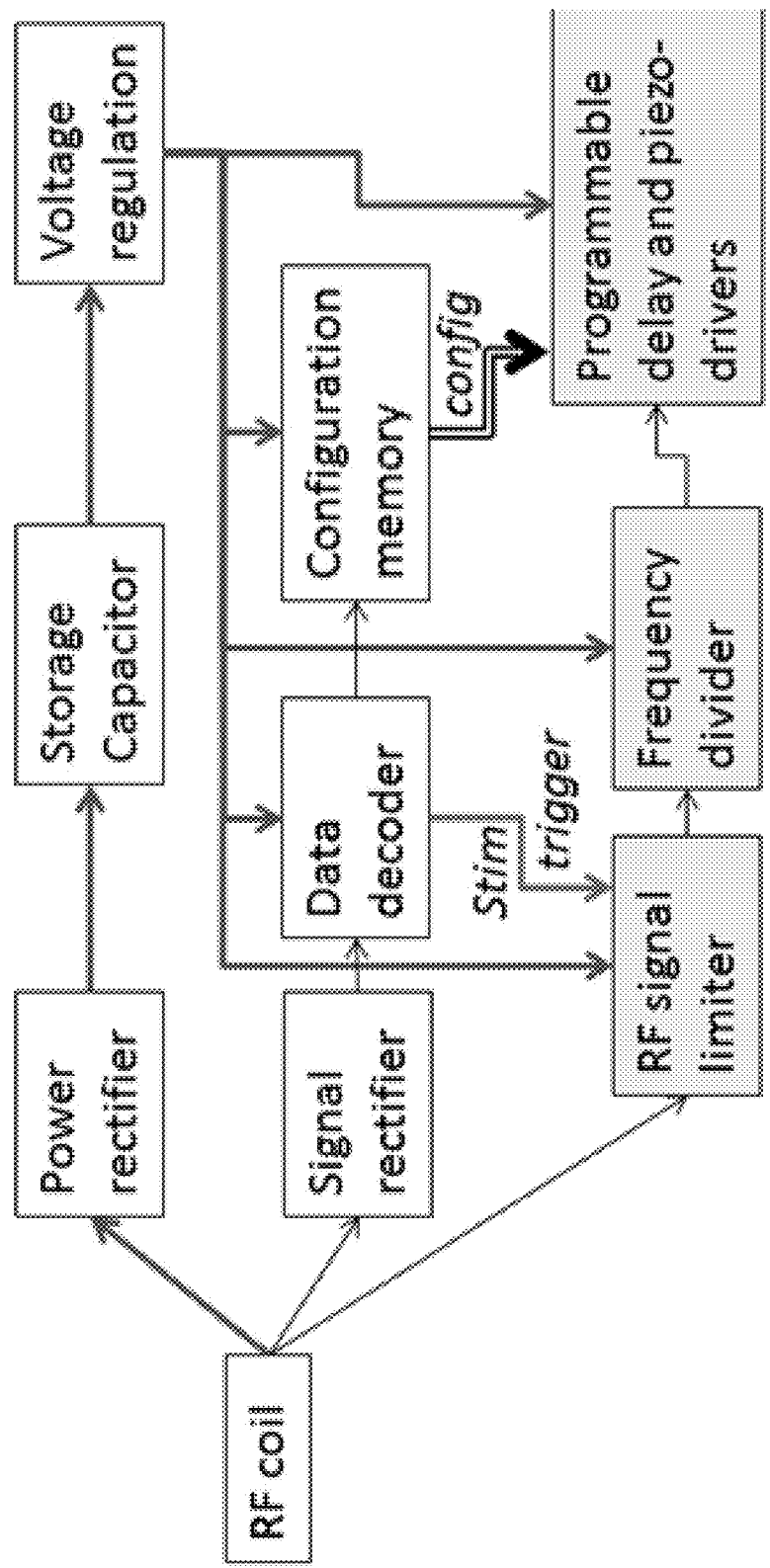
FIG. 13 shows an exemplary block diagram of electronic power and control functions of a SPARC.

FIG. 13 shows a block diagram of electronic power and control functions of a SPARC. Shaded blocks are only activated (and so only consume power) when a stimulation pulse is triggered.

Power Requirements:

Ultrasonic actuation will require driving the piezoelectric transducers' capacitance with a periodic voltage signal. Driving a total capacitance C, peak-to-peak drive $V_{pp}$, at a frequency F, requires $CV_{pp}^2 F/4$ power to drive. For an expected capacitance of 100 fF, voltage of 1 Vpp, and frequency of 100 MHz, this implies a power consumption of 2.5 μW. Furthermore, it is likely that this power can be delivered at a fairly low duty cycle: electrical stimulation of spiking neurons usually employs pulses of approximately 100 μs, while repeating at a rate of greater than once every 2 ms is unlikely to elicit additional response due to the refractory period of the neurons. Thus it is likely that the system can employ a duty cycle of 5% or less, likely significantly less. This would suggest that 1 μW average power delivered would be more than sufficient to power stimulation.

RF Power Delivery Challenges and Approach

The primary challenge with powering SPARCs with RF power is the very small cross-section of the disclosed SPARCs' pickup coils. This affects both the coil's inductance and the coupling coefficient between the external coil and pickup coil. A small coupling coefficient reduces the power picked up from the external coil while a small inductance reduces the impedance, and so voltage from the coil. In order to ensure that field from the external coil reaches the SPARCs, the external coil will need to be somewhat larger than the depth of the Vagus nerve below the skin. In this condition, the coupling coefficient, k, can be approximated as the ratio of the area of the two coils. Thus, for example, for an external coil with a diameter of 2 cm, and a SPARC coil with diameter of 300 μm, the coupling coefficient will be approximately 2·10⁻⁴. Thus, for a Watt of external RF power (about what a typical cell phone puts out) we can expect approximately 2 μW of power to be available to each SPARC, which, in principal would be sufficient to provide power for stimulation. The greater challenge, however, lies in providing the desired voltage.

Figure 14:
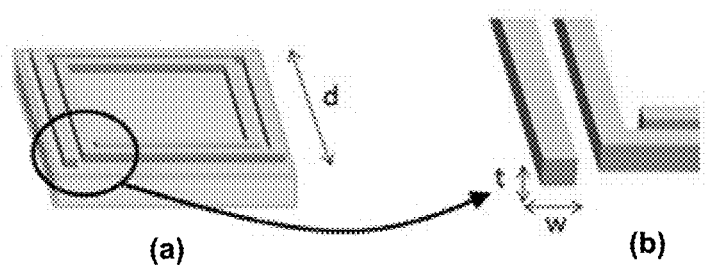
FIGS. 14(a)-14(b) show exemplary dimensions of integrated coil.

To see why this is challenging, it is necessary to see what a reasonable estimate for the inductance of the on-SPARC coil is. The inductance is estimated to be:

$$L_{int} \sim N^2 \mu \cdot d/2(\ln(8d/w)-2)$$

where d is the diameter of the coil, w is the width of the coil (as shown in FIGS. 14(a)-14(b)), and μ is the permeability, approximately 1.2×10⁻⁶ H/M. In the case of d=300 μm, and assuming w=15 μm (in order to avoid excessive series resistance) and 3 turns, this provides an inductance of about 5 nH. At 100 MHz, this implies an impedance of Z=3Ω. Since $V_{rms} = (P/Z)^{1/2}$, this, with 2 μW of power implies less than 1 V rms voltage. This is entirely insufficient to drive either the transducers directly, or any rectifier structure.

In order to increase this swing to useful levels without increasing the size of the SPARC, several modifications are necessary. First, to more precisely lay out the requirements on the two coils, we should first note that the voltage from the integrated coil will be:

$$V = j\omega L_{int} I_{int} + j\omega M I_{ext}.$$

Where M is the mutual inductance between the SPARC coil's inductance and the external inductance, and $M=k(L_{int}L_{ext})^{1/2}$. For the 2 cm-diameter external coil of above, with a single turn, and the integrated coil described, $L_{ext} \sim 40$ nH, so $M \sim 3$ pH. Since $I_{ext} \sim V_{ext}/(j\omega L_{ext})$, we can then approximate the voltage of the implanted coil, when it is unloaded (so that Iin=0) to be $V=V_{ext}(M/L_{ext})$. Thus even for a 100V external RF voltage, the internal voltage will only be 7.5 mV. This can be enhanced by resonating the on-chip coil with a capacitor, enhancing the voltage swing by the Q-factor of the inductor (assuming, reasonably, a high-Q capacitor). Similarly, the external coil can be resonated to reduce the amount of active current required to drive a given RF voltage across the external coil. In this case, then, $$V = Q_{int} Q_{ext} V_{ext} (M/L_{ext}).$$

Thus, the goal becomes getting high Q. Achieving an external inductor of about 20 should be possible, but the main challenge, in this case, is getting sufficient Q in the internal coil. For example, for the 5 nH coil described above, if the coil is 15 um wide, 2 um thick (what is reasonable for photolithography), and made of copper, then the expected series resistance will be approximately 2 Ohms, which at 100 MHz implies a $Q=\omega L/R$ of less than 2. In this case, still for a 100V external drive, we would expect only about 15 mV on the integrated coil, while actually consuming 22 Watts on the external coil, raising concerns about heating, for example. Q can be enhanced in a few different ways. One would be to increase the thickness of the integrated coil's metal. Achieving a square cross-section of 15 um×15 um would yield a Q of 13, but would likely require specialized fabrication, either for very thick copper growth, or physically looping wire around the outside of the SPARC. Another approach is to increase the number of turns, since resistance increases linearly with N, while inductance goes as the square of N. This approach has limited utility, since each extra turn in a planar coil is smaller and less effective, and so might also require additional fabrication techniques. The last approach is actually simplest, which is to simply increase the frequency of the RF signal, increasing the impedance due to inductance relative to series resistance. For example, for an otherwise identical setup to that described above, moving to 1 GHz increases internal voltage swing to 150 mV while reducing external power consumption to only 2 Watts.

Rectification and Voltage Boosting.

Figure 15:
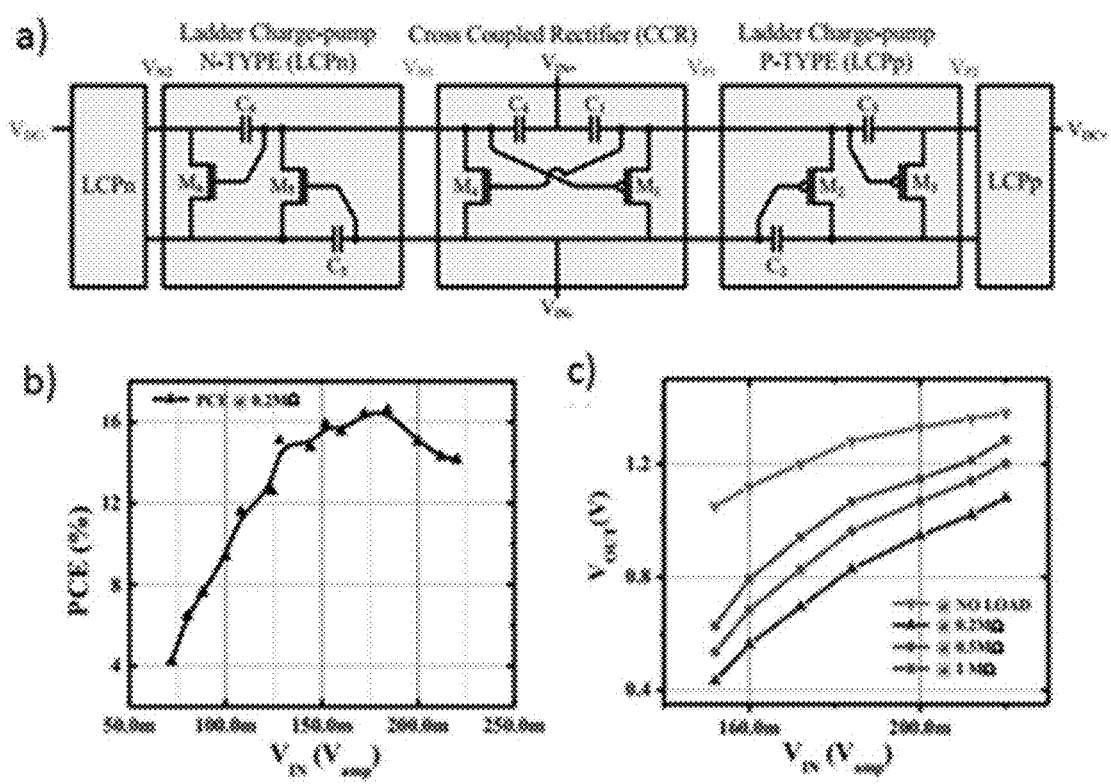
FIG. 15 shows preliminary results for one style voltage boosting rectifier: a) basic circuit topology, b) measured efficiency as a function of RF amplitude and c) DC voltage as function of RF amplitude.

Although much better, 150 mV is still not sufficient to directly drive the ultrasonic transducers, so it is necessary to include rectification and voltage boosting between the integrated coil and storage capacitor. A variety of reasonably efficient CMOS rectifiers have been developed, and in many cases, because the RF signal is AC-coupled in to them, boosted DC voltages much greater than the RF amplitude can be achieved simply by connecting them in series, DC-wise, but in parallel, AC-wise. Some embodiments have demonstrated a variant on this idea that works at especially low voltages, shown in FIG. 15. FIG. 15(a) shows an exemplary basic circuit topology. FIG. 15(b) illustrates measured efficiency as a function of RF amplitude and FIG. 15(c) shows DC voltage as function of RF amplitude. This approach can rectify RF signals of less than 150 mVm while producing 1 V-scale dc outputs, and can be scaled to arbitrarily high DC voltages by simply including more stages of charge pump.

Power Regulation:

One challenge for structures as small as a SPARC is that they must store sufficient DC energy for a give 100 us pulse of ultrasound in on-board capacitance. While most of the circuitry only requires 1 Volt DC, energy storage goes as $V^2C$. Thus, higher storage density requires either more capacitance, or increased storage voltage, with a square-law scaling advantage to increasing voltage. Thus voltages closer to 3V is employed. This, however requires an efficient method for stepping the voltage back down. Basic switched-capacitor circuits have been demonstrated which can efficiently step voltage down, and will be employed here for that purpose.

Data Demodulation:

In order to provide the required delays for the array of ultrasound generators, each SPARC must also be able to receive configuration bits from the external RF source. These bits will be encoded as low modulation index (~10%) amplitude modulation. To decode these bits, the RF signal must be rectified, and then high-passed to extract the modulation (which must therefore use a zero-DC scheme such as Manchester coding). These signals will then be amplified, and decoded. If a given packet includes a given SPARC' s address, then the payload data will be stored in memory to configure the delay of each ultrasound element. An alternate code will be used to trigger the short pulses of ultrasound required for stimulation.

Clock Extraction:

The RF signal will also provide the carrier wave for the ultrasound pulses used for neural stimulation. Because the RF frequency will likely need to be relatively high (1 GHz or higher) while the ultrasonic frequency may want to be significantly lower, a simple programmable CMOS frequency divider will be employed to step the frequency down to the desired value. Because such clock circuits tend to be somewhat higher power than the other circuits described (excepting the ultrasound drivers themselves) they will only be activated on the same duty cycle as the ultrasound output itself.

External Coil Design

Figure 16:
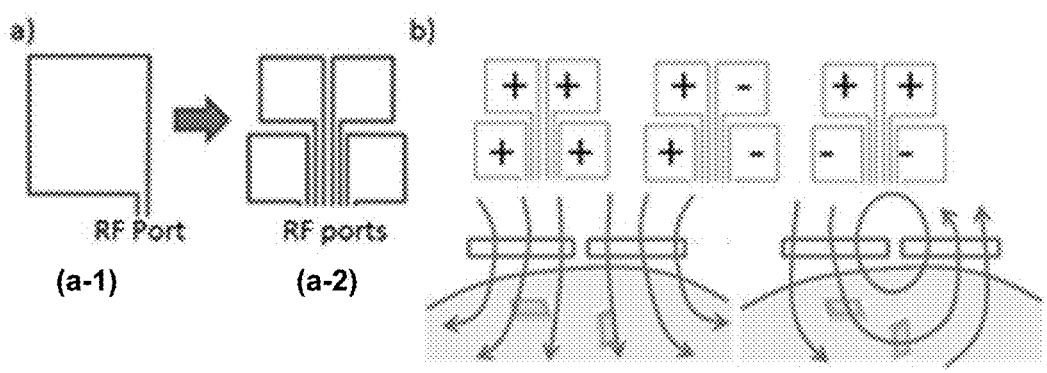
FIGS. 16(a-1), 16(a-2), and 16(b) show exemplary external coil configurations for reduced voltage and enhanced coupling.

One final challenge is actually delivering the external RF power in a compact, efficient, safe way. One potential issue is that multi-cm scale loop driven at 1 GHz inherently needs ~100 V to supply the signal strength we need. In order to reduce this voltage level to something smaller and safer, the loop can be split up into sub-loops. FIGS. 16(a-1) and 16(a-2) show an embodiment of four coils in parallel driven with 4× the current, ¼ the voltage deliver the same field intensity as a single larger coil. In this case each loop has the same current as the original loop, but ¼ the voltage. An extra benefit of this approach is that it allows shaping of the RF magnetic fields to efficiently couple to SPARCS in various orientations, simply by changing the relative phases of the sub-loops. FIG. 16(b) shows the sub-coils can be driven with different phases, allowing efficient coupling not only to SPARCs oriented in parallel to the skin, but also to those perpendicular. This in turn further eases the required precision of the SPARC injection process.

VI. High Intensity Ultrasonic Actuation of Needles for SPARC Delivery

Figure 17:
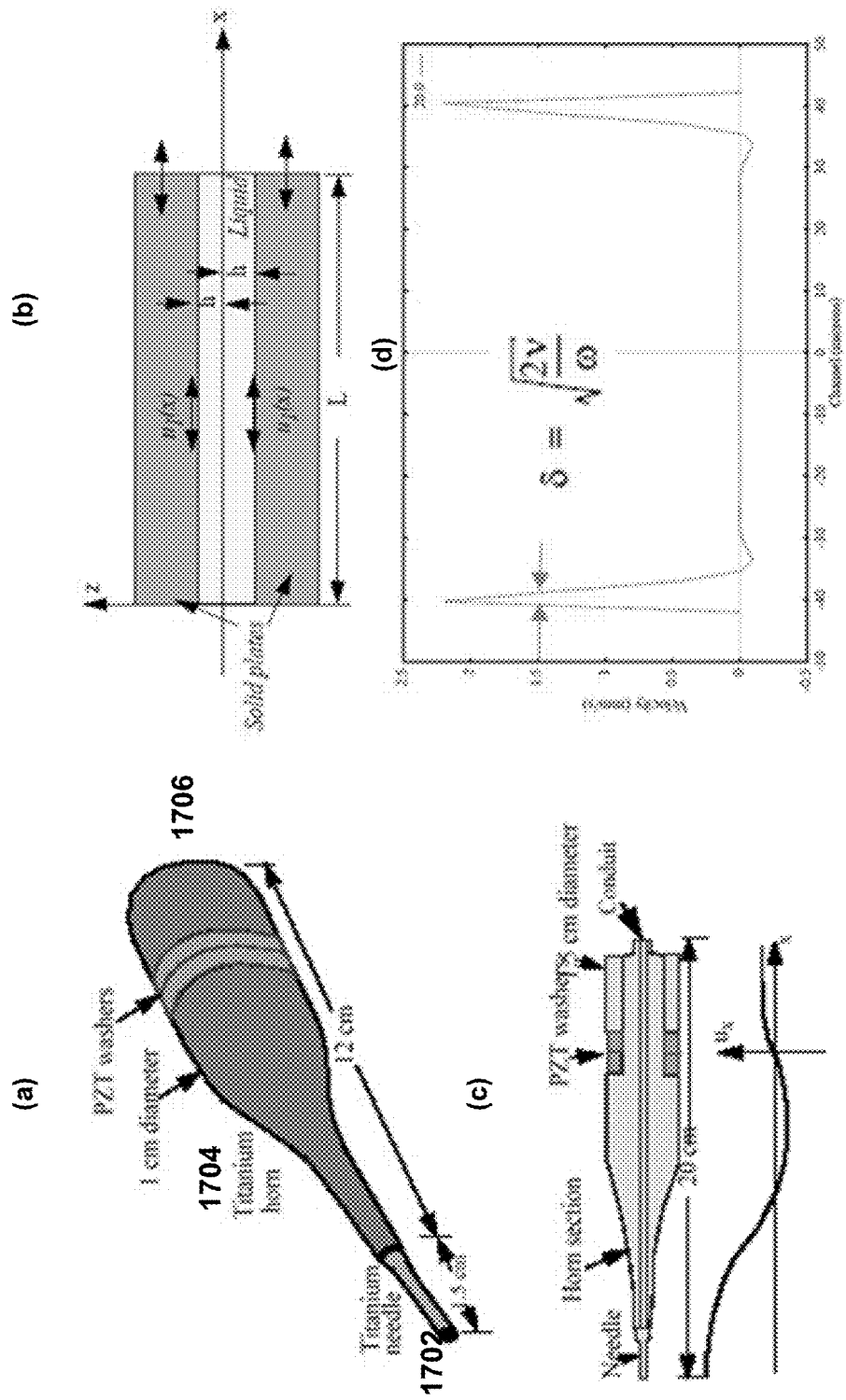
FIGS. 17(a)-17(d) show exemplary ultrasonic horns made in titanium and driven by PZT cylinders.

Injecting rectangular SPARC chips into the body will require innovation in delivering particles in a reliable way. The SPARCs coated with coatings should not get in abrasive contacts to remove the thin film coatings, or have the chiplets adhere to each other. Furthermore, in an injection particles can collect and form a barrier in the channel increasing the resistance to fluid flow, which further increases the chance of blockage. In order to address the challenges of channel blockage and wall resistance, ultrasonically driven horn actuators can be used as delivery tools for chiplets into tissue. Ultrasonic horns made in titanium 1704, and driven by PZT cylinders 1706 have been developed in SonicMEMS lab for ultrasonic surgical tools, as shown in FIGS. 17(*a*)-17(*d*). FIGS. 17(*a*)-17(*d*) show the ultrasonically vibrating needle 1702 produces a sinusoidal velocity on the needle surface on the outside and inside of the needle. FIGS. 17(*a*)-17(*d*) show the motion decays into the liquid on the length scale of the shear viscous length $\delta$. FIGS. 17(*a*)-17(*d*) illustrate that if a particle is placed in this cavity and touches the wall, the shear motion propels the particle away from the wall and centers the particles, or chiplets. Such tools are used in cataract surgery to cut and remove hardened eye lens. These horns with needles can be used to deliver chiplets guided by ultrasonic forces. The shear viscous depth of the motion of the wall into the fluid decays over a few shear viscous depths $\delta$, where $$\delta = \sqrt{\frac{2v}{\omega}}$$

where $v$ is the kinematic viscosity, and $\omega$ is the radian resonance frequency of the transducer. For example the shear viscous depth at 40 kHz in water at room temperature is ~3 µm. Some embodiments use the longitudinal resonators to develop a method to electronically deliver the chiplets into tissue. The shear viscous forces would carry the chaplets towards the tip with the walls ultrasonically lubricated, but would stop once the ultrasonic actuation is turned off. Hence a very fast method to deliver the chiplets into tissue can be realized.

Figure 18:
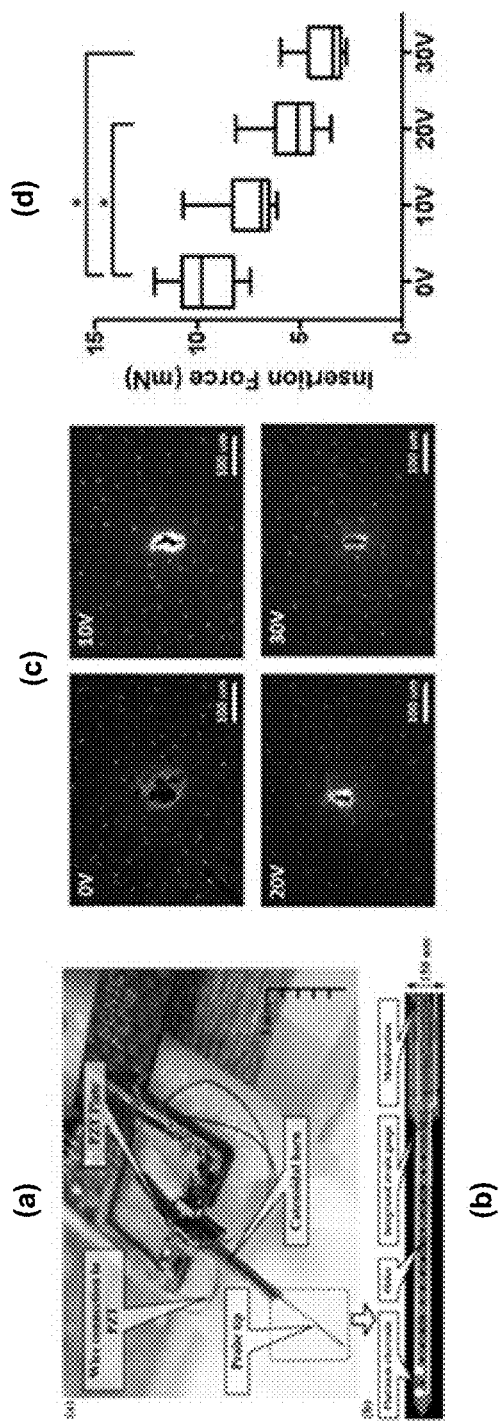
FIGS. 18(a)-18(d) show an exemplary ultrasonically actuated neural probe.

Ultrasonically driven needle force reduction: In addition to delivering chiplets reliably, another added benefit of sonic driving of the injection into the tissue is creating less damage to tissue and inducing less pain during the injection. An ultrasonically actuated neural probe, as shown in FIGS. 18(*a*)-18(*d*), has been demonstrated to minimize both mechanical stress and damage during and after insertion: (a) a miniature silicon horn with piezoelectric plates to drive the probe at its longitudinal resonance, (b) microphotograph of probe tip with integrated strain gauges and platinum recording sites, (c) histology slices under different PZT driving voltages, and (d) In vivo strain-gauge measured insertion force with different PZT driving voltages. (* p<0.05, n=6).

Reduction on insertion induced stress and damage can result in more reliable neural interface. One theory for ultrasound enhanced insertion in to tissue includes the following. The forces acting on the cutting edge of the probe can be written as $$f_o - F_x = -mA\omega^2 \sin(\omega t + \varphi) + k_1 \dot{x} + k_2 \dot{x}^2 \quad (1),$$

where $f_o$ is the tissue reaction force, $F_x$ is the user applied insertion force, m is the mass of the moving segment of the probes, $\omega$ is the ultrasonic drive frequency, $\dot{x}$ is the insertion speed, A is the amplitude of the oscillation, $k_1$ is viscous damping term and $k_2$ is nonlinear dependence on velocity, and $\varphi$ is the phase difference. The nonlinear dependence on velocity in this study was not observed and hence assumed negligible. The probe insertion velocity can further be written as $$V_{insertion} = V_{DC} + V_o e^{j\omega t} \quad (2),$$

where the first term, $V_{DC}$, is the insertion stage velocity, ~2 mm/s, and $V_o e^{j\omega t}$ is the velocity of ultrasonic actuation. This velocity is $|V_o|=|2\pi f U_o|$, where f is the half wave length longitudinal resonance frequency of the probe, 418.13 kHz, and $U_o$ is the measured displacement from optical interferometer. 82 nm to 246 nm displacement were measured with PZT driving voltage from 10 Vpp to 30 Vpp. The $V_o$ is in the range of 215 mm/s to 645 mm/s, which is two order of magnitude higher than the insertion stage velocity. This high velocity vibration at the tip could help cutting the tissue with less force. The equation from (1) was fit by using a nonlinear regression mean-squared minimization function with experiment results from different percentage of agar gels, PZT driving voltages, and insertion speeds as $$F_t = (5.9 \pm 0.5)Y + (1.2 \pm 0.3)Y\dot{x} - (0.3 \pm 0.2)V - (13.9 \pm 1.0) \quad (3),$$

where $F_t$ is the measured force transducer force in milliNewton, and Y is the substrate percent agarose, and V is the PZT driving voltage in volts. The calculated insertion force without ultrasonic actuation for 2% agar gel is 12.9 mN, this is comparable with the result from for 100 um diameter flat punch stainless steel cylindrical probe without removing dura and pia mater (11.594 mN) and our in vivo measurement result. While applying the ultrasonic actuation through the horn, the high velocity vibration on the tip can reduced the penetration force. With sonic drive, the zone of damage is less as cutting is confined to the tip. According to (3), the insertion force can be reduced by 3 to 9 mN with 10 Vpp to 30 Vpp driving voltage. The estimated force reduction agrees with our in-vivo measurement results. Ultrasonic insertion causes the tissue-probe interface to have reduced insertion force by a factor of 2.6 and net-stress by a factor of 1.5, due to the ultrasonic cutting leading to less average stress and providing stress relief. Quantified damaged area in 30 µm thick histological sections indicating that insert electrode ultrasonically caused less damaged area by a factor of 1.65. Following the above results, using ultrasonic cutting, the force require to cut through skin will likely to be reduced, enabling easier penetration into tissue towards the Vagus nerve for injection of the chiplets. Some embodiments also integrate strain gauges into the metal ultrasonic delivery system to sense the Vagus nerve such that the delivery of the chiplets can be accomplished right in front of the nerve.

VII. Animal Model Development: Adult Stress Models Chronic Mild Stress

The chronic mild stress (CMS) paradigm has been established as a model that is sensitive to chronic antidepressant treatment and emphasizes the predominant role of stress in the etiological cause of depression. The CMS paradigm involves the exposure of animals to a series of mild and unpredictable stressors (isolation or crowded housing, food or water deprivation, disruption of dark-light cycle, tiling of home cages, dampened bedding, etc.) during at least 2 weeks. CMS has been reported to result in long lasting changes of behavioral, neurochemical, neuroimmune, and neuroendocrinological parameters resembling dysfunctions observed in depressed patients. CMS model is one of the best validated animal models of depression in preclinical antidepressant evaluation, for its good etiological validity and predictive validity.

The chronic mild stress paradigm includes 2 h of paired caging, 3 h of tilted cage (45 degrees), 18 h of food deprivation immediately followed by 1 h of restricted access to food (5 micropellets), 2×18 h of water deprivation immediately followed by 1 h exposure to an empty bottle, 21 h of wet cage (200 ml water in 100 g sawdust bedding), and 36 h of continuous light.

Early Life Stress Models

Early adverse experiences such as traumatic life events in childhood result in an increased sensitivity to the effects of stress later in life and influence the individual vulnerability to stress-related psychiatric disorders such as depression. The most widely used model is the maternal separation paradigm of early life deprivation, in which pups are separated from the dam for 1-24 h per day during the first two postnatal weeks. Maternal separation results in increased anxiety- and depression-like behaviors and increased hypothalamic-pituitary-adrenocortical (HPA) axis response in adulthood. While the exact psychological nature of the effects of postnatal maternal separation is not fully understood, the paradigm supports the utility of rodent models for studying the neurobiological basis of the effects of early life stress on emotion and reward-related behavior.

The Maternal Separation procedure includes daily separation of the litters from the dam for 3 hours from PND2 through 14. Normal handled animals will be separated daily for 15 min from PND2 through 14. For both groups, the dam will be removed from the maternity cage while she is off the nest and placed in a separate cage, assigned to her individually throughout the separation process. Then, the pups will be removed as complete litters, and each litter will be placed in a plastic container lined with standard bedding material. The litters will return to the same plastic container at every separation session.

Behavioral Testing

Rats will be handled for 3 days prior to the behavioral test day. On the test day, rats will be brought to the test room for at least one hour before the test. Behavioral tests will be conducted in sequential order of Sucrose Preference Test (SPT), Open Field Test (OFT), Elevated Plus Maze (EPMT), Light Dark Box (LDB) and Forced Swimming Test (FST) with one to two day intervals between the tests.

Sucrose Preference Test (SPT)

This test includes a 48 hour training session and a 1 hour test session conducted 24 hours after the training session. In the training session, singly housed rats will be trained to drink sugar water in a cage containing two bottles, one bottle containing a 1% sucrose solution and another bottle containing tap water for 48 hours. The bottles will be placed to the left and right side of the feeding compartment, respectively and will be switched every 12 hours to prevent possible effects of side preference in drinking behavior. After the training session, only tap water will be provided for 6 hours. Then food and water will be withheld from rats for 18 hours. Subsequently, in the test session, rats will be provided access to two bottles with 1% sucrose solution and water, respectively, for one hour. Sucrose preference will be analyzed according to the formula below: Sucrose preference (SP)=[sucrose intake (g)/(sucrose intake (g)+water intake (g))]×100. The proportion of rats in each group with an SP value of ≥75% will be then counted and compared using the Chi-square test.

Open Field Test (OFT)

The open field apparatus includes an arena (100 cm×100 cm×40 cm) made of black plastic, which is dimly illuminated (corner: 6 lx; center: 12 lx). A rat is gently placed into the corner of the field, and allowed to explore the arena for 30 minutes. Movements are recorded by a video camera mounted above the arena, and analyzed using the video tracking system. The number of entries into the center, the percentage time in the center, the total distance traveled and the proportion traveled in the center during the test period will be measured.

Elevated Plus Maze (EPM) Test

The EPM apparatus, made of black polypropylene, includes two opposite closed and two opposite open arms (10 cm width) with 30 cm high walls and a center area (10×10 cm), elevated 50 cm above the floor. Rats will be placed individually in the center of the maze facing an open arm and will be allowed 5 minutes of free exploration. The movements of the animals during the 5-minute test period will be tracked by a video camera positioned above the center of the maze and analyzed using Ethovision (Noldus Information Technology) video tracking system to evaluate the time spent the open arms, percentage moved in open arm and total distance moved during the 5-minute test time.

Light Dark Box (LDB) Test

The apparatus for this test includes two equally sized compartments (h×w×l: 24×25×33 cm) connected by an 8×8 cm opening. One compartment will be painted black and covered with a black lid (dark box). The other compartment will be opaque and remained uncovered during the test (light box). An opaque black Plexiglas with a door separated the two boxes. Inside the light box will be illuminated by a 30 lux light. Inside the dark box there will be no appreciable illumination (<2 lux). On test days, rats will be moved to the test room 60 minutes prior to testing. Assessments will be performed between 10 a.m. and 3 p.m. To start the test, the rat will be placed in the center of the light box facing away from the door to the dark box and allowed to freely explore the apparatus for 5 min. The movements of the animals during the 5 minute test period will be tracked by a video camera positioned above the center of the light dark box and analyzed using the video tracking system (Noldus Information Technology).The data of behavior analysis includes the percentage of time spent in the light box and dark box and the number of chamber transitions, defined as at least half of the animal's body from one chamber to the next.

Forced Swimming Test (FST)

A clear Plexiglas cylinder (65 cm tall×25 cm diameter) will be filled to 48 cm with 25° C. water. On the training day, the rats will be placed in the cylinder for 10 minutes and then remove from the water. 24 hours later, rats will be retested for 5 minutes under identical conditions and their behavior recorded on videotape. Videotapes will be scored by a blind examiner using a time-sampling technique: the behavior at the end of each 5-second period will be categorized as one of the following: 1) immobility: the rat remains floating in the water without struggling and made only those movements necessary to keep its head above water; 2) swimming: the rat displays active swimming motions, more than necessary to merely maintain its head above water, e.g. moving around in the cylinder; 3) climbing: the rat displays active movements with its forepaws in and out of the water, usually directed against the walls.

VII. Exemplary Implementations: Phases

| Metrics | Phase I | Phase II |
|---|---|---|
| Ultrasonic stimulation intensity (W/cm$^2$) - *1 | 50 (off chip) | 1 (SPARC) |
| Ultrasonic stimulation resolution (um) - *2 | 200 | 25 |
| Ultrasonic duration to stimulation (us) - *3 | 500 | 100 |
| Range of RF transfer - *4 | 0.5 cm | 5 cm |

-continued

| Metrics | Phase I | Phase II |
|---|---|---|
| SPARC power transfer (microWatts) - *5 | 10 | 20 |
| Sonic delivery of chiplets (distance to target) (um) -*6 | 500 | 50 |

*1. The 50 W/cm$^2$ is an example of intensity that all of our frequency range transducers can achieve with wall power. The metric is intended to prove that we can in-fact excite nerves with ultrasound over a very wide range of frequencies without regard for electrical power needed. The 1 W/cm$^2$ intensity is for phase II for SPARCs to be able to stimulate nerves, with the power SPARCs will be able to generate in Phase II.
*2. Stimulation resolution: indicates how finely the US peak intensity can be focused to give a minimal set of axons to be stimulated. In phase I this is 200 um providing control spatial control of about 20% as the Vagus nerve is about a 1-mm in diameter. This will be still far better than any other non-electrical probe based spatial stimulation approach. In phase II we will focus to 25 um by working at high frequencies from 100 MHz upwards to give finer resolution.
*3. Stimulation duration: This duration is indicative of the energy needed to stimulate the nerves, as the Intensity times the duration gives the total energy delivered to tissue. In Phase I we aim for 500 us as we are not sure of what time the nerves will require. Preliminary experiments in lab at low frequencies seem to produce reliable results even with 600 us stimuli. In phase II we will optimize the stimulation process, by virtue of having identified new results, to 100 uS enabling very low power SPARCS to be able to stimulate.
*4 & *5. Range of RF transfer: In FIG. 1 we envision the collar delivering the RF power to tissue imbedded SPARCs. In phase I we will push for 10 uW of RF power transferred over 0.5 cm distance. In phase II, we will optimize by picking the right frequency and RF design of transmit antenna to increase power transfer to 20 uW/SPARC over 5-cm distance.
*6Ultrasonically induced chiplet delivery close to the Vagus nerve is important to ensure high resolution at high frequencies, while overcoming the higher loss at higher frequencies. We aim to get the chiplets close to 500 um of the nerve in phase I so low frequency excitation at a few MHz to 50 MHz would still reach axons within the nerve. In Phase II we will push to 50 um where 100-500 MHz t 1 GHz excitations should be able to reach the nerve for higher stimulation resolution.

IX. Considerations

Ultrasonic stimulation of Vagus nerve: Due to the boundary conditions presented by the body in the form of tissue in-homogeneities, US pulses may scatter sonic energy that affects the focus on spots, and/or tissue absorption may be too high. A consideration can include to lower the frequency to increase wavelength to reduce scattering. This may create a tradeoff between stimulation resolution and stimulation intensity. We can also augment the internally generated stress by outside skin placed sonic transducers, operating at a much lower frequency to add strain fields to help the internal chips achieve the thresholds needed to trigger the nerves.

We can also form a distributed sonar network where different SPARCs operate at lower operation frequency, perhaps outside of the resonant modes of the transducers, to add coherently within the nerve. Each SPARC would listen to other SPARCs to locate itself in position with respect to others and determine the proper phasing by communicating with the external device.

SPARC placement from the nerve for focusing—The placement accuracy may depend on how close can the needle get to the Vagus nerve under ultrasonic imaging. We can also make insert a force microprobe, as shown in Fig Probe, to co-enter the tissue to find the tissue-nerve boundary, and then insert the chiplet driver to the location of the probe. This may be more complicated and maybe a longer procedure. Another approach to address this possible issue is to inject many SPARCs with the expectation that many of them are not effective in stimulation.

Power transfer to SPARCs: The size of the SPARC chips may limit the power transfer to the chips, e.g., due to limited mutual inductance with the external device. Potential area disadvantages can be fought by development of on-chip higher value inductors by adding magnetic materials, and making 3D etched capacitors to store higher energy to be released in pulse modes. Another approach may include the use of integrated piezo on SPARCs to harvest ultrasonic energy from outside the body to power SPARCS, e.g., which may include direct contact for treatment that could limit the use of on-demand electrical prescriptions.

Biocompatibility of SPARCs: In some implementations, the chips can be coated with organic coatings such as Parylene™. Other example, films and/or coating structures can be used to address chip topography and biochemical reactions in the body. In some implementations, for example, the coating can include secondary metal coatings of platinum, carbon, and potentially even graphene to provide a nanoscale approach to prevent ions from diffusing into SPARCs.

Animal model for Depression: Animal models can include excessive variability. This may limit the interpretation of the data obtained by stimulating the Vagus nerve. To address this, the exemplary implementations may include a large number of rats tested to get statistical significance.

SPARC motion: SPARC chips may be able to move around the Vagus nerve due to physics of firing pulse momentum into tissue and other bio phenomenon. This issue can be addressed by attaching tissue binding molecules onto SPARC coatings.

Figure 19:
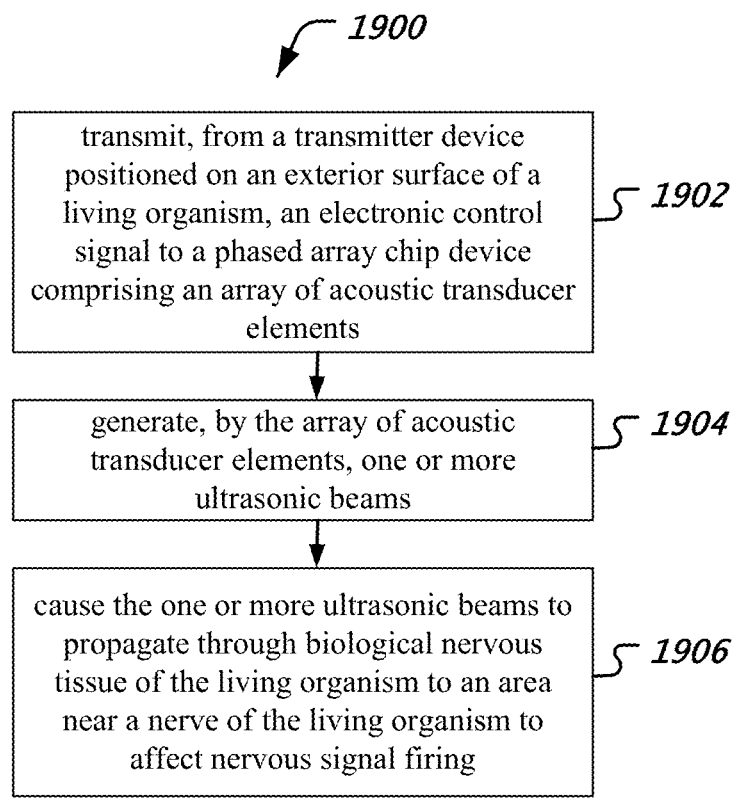
FIG. 19 is a flowchart for acoustic nerve stimulation.

FIG. 19 shows an example flowchart 1900 for acoustic nerve stimulation. The method 1900 of optical communication may be implemented using a collar-mounted transmitter device 104 and a sonic phase array chip device 102 depicted in FIG. 1.

The method 1900 includes, at 1902, transmitting, from a transmitter device positioned on an exterior surface of a living organism, an electronic control signal to a phased array chip device comprising an array of acoustic transducer elements. In some embodiments, the array of acoustic transducer elements include piezoelectric materials comprising at least one of aluminum nitride (AlN), lead zirconate titanate (PZT), or Poly Vinyl DiFluride (PVDF) configured as thin films.

The method of 1900 includes, at 1904, generating, by the array of acoustic transducer elements, based on the control signal, one or more ultrasonic beams. In some embodiments, the array of acoustic transducer elements operate in a frequency range of 5 KHz to 3 GHz for the signal generation.

The method of 1900 includes, at 1906, causing the one or more ultrasonic beams to propagate through biological nervous tissue of the living organism to an area near a nerve of the living organism to affect nervous signal firing. In some embodiments, the biological nervous tissue includes the Vagus nerve and affecting nervous signal firing comprises both inhibiting and increasing nerve firing rates of the Vagus nerve.

Figure 20:
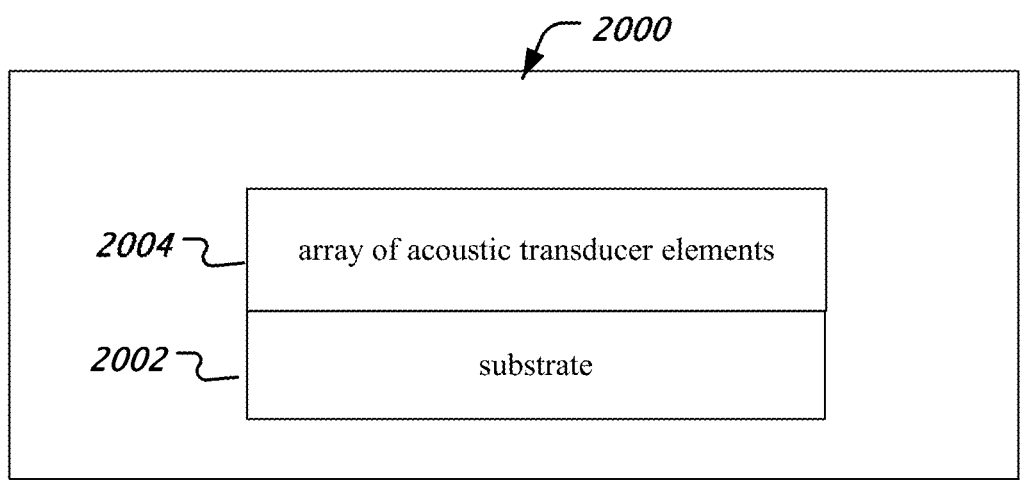
FIG. 20 is a block diagram of an exemplary ultrasonic phased array chip.

FIG. 20 shows an example ultrasonic phased array chip 2000 for acoustic nerve stimulation. The chip comprises a substrate 2002, and an array of acoustic transducer elements 2004 is placed on the substrate 2002. The array of acoustic transducer elements are operable to generate ultrasonic beams based on electronic control signals, capable to propagate the ultrasonic beams through biological nervous tissue to affect nervous signal firing.

Implementations of the subject matter and the functional operations described in this patent document and attached appendices can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document and attached appendices contain many specifics, these should not be construed as limitations on the scope of any invention or of what may be claimed, but rather as descriptions of features that may be specific to particular embodiments of particular inventions. Certain features that are described in this patent document and attached appendices in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendices should not be understood as requiring such separation in all embodiments.

Only a few implementations and examples are described and other implementations, enhancements and variations can be made based on what is described and illustrated in this patent document and attached appendices.

What is claimed are techniques and structures as described and shown, including:

1. A system for acoustic nerve stimulation, comprising:
   an ultrasonic phased array chip device deployable into a living organism, the ultrasonic phased array chip device including a substrate and an acoustic signaling module on the substrate, the acoustic signaling module including an array of acoustic transducer elements configured to generate ultrasonic beams based on electronic control signals and configured to propagate the ultrasonic beams through biological nervous tissue to affect nervous signal firing; and
   a transmitter device wearable on an exterior of the living organism, wirelessly couplable with the ultrasonic phased array chip device to transmit the electronic control signals.
   wherein the array of acoustic transducer elements operates in a frequency range greater than 100 MHz up to 3 GHz.

2. The system of claim 1, wherein at least some elements of the array of acoustic transducer elements are driven by different phases to direct the ultrasonic beams in different directions.

3. The system of claim 1, wherein the array of acoustic transducer elements include piezoelectric materials comprising at least one of aluminum nitride (AlN), lead zirconate titanate (PZT), or Poly Vinyl DiFluride (PVDF) configured as thin films.

4. The system of claim 1, wherein the biological nervous tissue includes a Vagus nerve and the generated ultrasonic beams are capable of inhibiting and/or increasing nerve firing rates of the Vagus nerve.

5. The system of claim 1, wherein the array of acoustic transducer elements operate in a frequency range greater than 100 MHz up to 1 GHz to achieve spatial accuracy such that a generated ultrasonic beam hits one axon at a time in the Vagus nerve.

6. The system of claim 1, wherein the ultrasonic phased array chip device comprises multiple ultrasonic phased array chip devices that are deployable into a target area around the biological nervous tissue by injection from a needle.

7. The system of claim 1, wherein the ultrasonic phased array chip device is injected into the living organism and placed within a sonic delivery distance to a target using an ultrasonically actuated needle.

8. The system of claim 1, wherein the transmitter device further comprises one or more RF antennas configured to power the ultrasonic phased array chip device.

9. A method for acoustic nerve stimulation, comprising:
injecting a phased array chip device comprising an array of acoustic transducer elements into a living organism to an area near a nerve of the living organism;
transmitting, from a transmitter device positioned on an exterior surface of the living organism, an electronic control signal to the phased array chip device comprising the array of acoustic transducer elements; generating, by the array of acoustic transducer elements, based on the control signal, one or more ultrasonic beams, wherein the array of acoustic transducer elements is operable in a frequency range greater than 100 MHz up to 3 GHz; and
causing the one or more ultrasonic beams to propagate through biological nervous tissue of the living organism to the area near the nerve of the living organism to affect nervous signal firing.

10. The method of claim 9, wherein at least some elements of the array of acoustic transducer elements are driven by different phases to direct the one or more ultrasonic beams in different directions.

11. The method of claim 9, wherein the array of acoustic transducer elements include piezoelectric materials comprising at least one of aluminum nitride (AlN), lead zirconate titanate (PZT), or Poly Vinyl DiFluride (PVDF) configured as thin films.

12. The method of claim 9, wherein the biological nervous tissue includes a Vagus nerve and affecting nervous signal firing comprises inhibiting and/or increasing nerve firing rates of the Vagus nerve.

13. The method of claim 12, wherein generating the ultrasonic beams comprises operating the array of acoustic transducer elements in a frequency range greater than 100 MHz up to 1 GHz to achieve spatial accuracy of hitting one axon at a time in the Vagus nerve.

14. An ultrasonic phased array chip for acoustic nerve stimulation, comprising:
a substrate; and
an array of acoustic transducer elements on the substrate, the array configured to generate ultrasonic beams, wherein the array of acoustic transducer elements operates in a frequency range greater than 100 MHz up to 3 GHz and configured to affect signal firing of a target nerve area.

15. The ultrasonic phased array chip of claim 14, further comprising a phase rotator under each element of the array of acoustic transducer elements.

16. The ultrasonic phased array chip of claim 14, wherein at least some elements of the array of acoustic transducer elements are driven with different phases to direct the ultrasonic beams at different directions.

17. The ultrasonic phased array chip of claim 14, wherein the target nerve area includes a Vagus nerve.

18. The ultrasonic phased array chip of claim 14, wherein the array of acoustic transducer elements operate in a frequency range greater than 100 MHz to 1 GHz to achieve a spatial accuracy of hitting one axon at a time in the target nerve area to inhibit and/or increase nerve firing rates.

19. The ultrasonic phased array chip of claim 14, further comprising a charging coil embedded in the substrate to wirelessly receive power.

20. The ultrasonic phased array chip of claim 14, further comprising a clock circuit that is activated only when affecting signal firing of the target nerve area.

21. The ultrasonic phased array chip of claim 14, wherein the ultrasonic beams have an intensity in a range between 5 to 300 W/cm2.

* * * * *